(12) United States Patent
Kottayil et al.

(10) Patent No.: US 11,291,672 B2
(45) Date of Patent: Apr. 5, 2022

(54) BETAMETHASONE ORAL SPRAY FORMULATION AND METHOD OF USE TO TREAT ATAXIA

(71) Applicant: GRACE THERAPEUTICS LLC, North Brunswick, NJ (US)

(72) Inventors: S. George Kottayil, West Windsor, NJ (US); Amresh Kumar, Plainsboro, NJ (US); Prasanna Sunthankar, West Windsor, NJ (US); Vimal Kavuru, Holmdel, NJ (US)

(73) Assignee: GRACE THERAPEUTICS INC., North Brunswick, NJ (US)

( * ) Notice: Subject to any disclaimer, the term of this patent is extended or adjusted under 35 U.S.C. 154(b) by 0 days.

(21) Appl. No.: 15/404,859

(22) Filed: Jan. 12, 2017

(65) Prior Publication Data

US 2017/0196889 A1     Jul. 13, 2017

Related U.S. Application Data

(60) Provisional application No. 62/277,707, filed on Jan. 12, 2016.

(51) Int. Cl.
| | | |
|---|---|---|
| *A61K 31/573* | (2006.01) | |
| *A61K 47/12* | (2006.01) | |
| *A61K 9/08* | (2006.01) | |
| *A61K 47/02* | (2006.01) | |
| *A61K 9/00* | (2006.01) | |
| *A61K 47/26* | (2006.01) | |

(52) U.S. Cl.
CPC ............ *A61K 31/573* (2013.01); *A61K 9/006* (2013.01); *A61K 9/0053* (2013.01); *A61K 9/0095* (2013.01); *A61K 9/08* (2013.01); *A61K 47/02* (2013.01); *A61K 47/12* (2013.01); *A61K 47/26* (2013.01)

(58) Field of Classification Search
CPC .... A61K 31/573; A61K 9/0053; A61K 9/006; A61K 9/08; A61K 47/02; A61K 47/12; A61K 47/26
See application file for complete search history.

(56) References Cited

U.S. PATENT DOCUMENTS

| | | |
|---|---|---|
| 6,495,120 B2 | 12/2002 | McCoy et al. |
| 2004/0180870 A1 | 9/2004 | Hanna |
| 2005/0014073 A1 | 6/2005 | Watts et al. |
| 2005/0136116 A1 | 6/2005 | Whitehead |
| 2005/0153946 A1 | 7/2005 | Hirsh et al. |
| 2007/0248548 A1* | 10/2007 | Blondino ............... A61K 38/28 424/44 |
| 2013/0303498 A1 | 11/2013 | Pipkin et al. |
| 2014/0311482 A1 | 10/2014 | Levitt |
| 2015/0133517 A1* | 5/2015 | Vangara ................. A61K 47/10 514/397 |
| 2015/0258119 A1 | 9/2015 | Kandavalli et al. |

FOREIGN PATENT DOCUMENTS

| | | | | |
|---|---|---|---|---|
| EP | 2735305 A1 | 11/2013 | | |
| EP | 2735305 A1 * | 5/2014 | ........... | A61K 9/0019 |
| JP | 2007275197 A | 10/2007 | | |
| WO | WO-0047203 A1 * | 8/2000 | ............ | A61K 9/006 |
| WO | 2005/102287 A2 | 11/2005 | | |
| WO | WO-2008057773 A2 * | 5/2008 | ............ | A01N 47/44 |

OTHER PUBLICATIONS

Zannolli et al (Year: 2012).*
Perisco et al (Year: 2006).*
Buoni et al (Year: 2006).*
Kviecinski et al (Year: 2008).*
Zannolli (Year: 2012).*
A. J. Winfield et al. "Pharmaceutical Practice, International Edition E-Book", Fourth Edition, p. 339; Year: 2009.
International Search Report from corresponding European Patent Application No. EP 17 73 8920 dated Aug. 30, 2019.
Zannoli et al., "A Randomized Trial of Oral Betamethasone to Reduce Ataxia Symptoms in Ataxia Telangiectasia" Movement Disorders, vol. 27, No. 10, pp. 1312-1316 (2012), abstract, p. 1313, Figure 1A.
International Search Report from International PCT Application No. PCT/US2017/013173 dated Apr. 4, 2017.
Notification Concerning Transmittal of International Preliminary Report on Patentability from International PCT Application No. PCT/US2017/013173 dated Jul. 26, 2018.
International Preliminary Report on Patentability from International PCT Application No. PCT/US2017/013173 dated Jul. 17, 2018.

* cited by examiner

*Primary Examiner* — Jeffrey S Lundgren
*Assistant Examiner* — Ibrahim D Bori
(74) *Attorney, Agent, or Firm* — Davidson, Davidson & Kappel, LLC

(57) ABSTRACT

A stable oral spray formulation comprising a glucocorticoid together with other excipients is disclosed. In preferred embodiments, the spray formulation is used to treat neurological disorders such as ataxia by being sprayed in an effective dose into the mouth of a patient.

25 Claims, 5 Drawing Sheets

BETAMETHASONE ORAL SPRAY FORMULATION AND METHOD OF USE TO TREAT ATAXIA

FIELD OF THE INVENTION

The invention is directed in part to an ambient temperature stable oral spray formulation of glucocorticoid steroid for treating neurological disorders, and in part to an oral betamethasone spray formulation for the treatment of ataxia telangiectasia.

BACKGROUND OF THE INVENTION

Betamethasone is a glucocorticoid and belongs to a group of drugs called corticosteroids. The approved indications of betamethasone include numerous steroid responsive diseases, including allergic states, dermatologic diseases, endocrine disorders, gastrointestinal diseases, hematologic disorders, parasitic conditions, rheumatic disorders, cancer, and other conditions related to the nervous system, eyes, kidneys, and lungs.

Betamethasone has been approved in the U.S. in multiple forms (oral solid, oral liquid, injection, and topical), both as a free base (NDAs 12657, 14215, 17561 and 14762, respectively), as an injectable in combination with betamethasone acetate (NDA 14602), and in a number of salt forms. The innovator betamethasone base product was sold under the trade name Celestone® by Merck & Co./Schering (Merck) and the innovator continues to market the combination product under the trade name Celestone® Soluspan®. There is also a generic form of the combination available. Over the past years, all of the betamethasone oral product NDAs have been withdrawn (not for safety or efficacy reasons) as these products are no longer marketed.

Until recently, betamethasone was available in the U.S. as an oral solution (Celestone® Oral Solution in the form of betamethasone base, containing 0.6 mg betamethasone in each 5 mL, for a variety of allergic states (e.g., asthma, atopic dermatitis, contact dermatitis, drug hypersensitivity reactions, allergic rhinitis, serum sickness), dermatologic diseases (e.g., bullous dermatitis herpetiformis, exfoliateive erythroderma, mycosis fungoides, pemphigus, severe erythema multiforme), endocrine disorders (congenital adrenal hyperplasia, hypercalcemia associated with cancer, numsuppurative thyroiditis), gastrointestinal diseases (regional enteritis and ulcerative colitis), hematologic disorders (e.g., autoimmune hemolytic anemia, Biamond-Blackfan anemia, idiopathic thromobocytopenic purpura, pure red cell aplasia, selected cases of secondary thrombocytopenia), neoplastic diseases, nervous system conditions or diseases (e.g., multiple sclerosis, cerebral edema, craniotomy, head injury), ophthalmic diseases (e.g., sympathetic opthalmia, temporal arteritis, uveitis and ocular inflammatory conditions unresponsive to topical tcorticosteroids), renal diseases, respiratory diseases (e.g., berylliosis, fulminating or disseminated pulmonary tuberculosis, idiopathic eosinophilic pneumonias, sympatomatic sarcoidosis), rheumatic disorders (e.g., acute gouty arthritis, acute rhematic carditis, ankylosing spondylitis, psoriatic arthritis, rheumatoid arthritis, dermatomyositis, polymyositis, systemic lupus erythematosus), trichinosis, etc. Celestone® Oral Solution contained alcohol (less than 1%), citric acid, FD&C Red No. 40, FD&C Yellow No. 6, flavors, propylene glycol, sodium benzoate, sodium chloride, sorbitol, sugar and water.

Betamethasone is also available as an injectable suspension (e.g., Celestone® Soluspan® Injectable Suspension) in a strength of 3 mg/ml (equivalent to 3 mg/base/ml), which has similar indications. The injectable suspension includes a combination of betamethasone acetate and betamethasone sodium phosphate as the active ingredient.

In addition to the above, betamethasone is commercially available in the U.S. in a variety of forms, including aerosol, foam (e.g., in the form of betamethasone valerate); as a lotion, topical suspension, ointment or cream (e.g., in the form of betamethasone dipropionate). Betamethasone Sodium Phosphate and Betamethasone Acetate Injectable Suspension, USP is a sterile aqueous suspension containing betamethasone 3 mg per milliliter as betamethasone sodium phosphate, and betamethasone acetate 3 mg per milliliter. Inactive ingredients per mL: dibasic sodium phosphate 7.1 mg; monobasic sodium phosphate 3.4 mg; edetate disodium 0.1 mg; and benzalkonium chloride 0.2 mg as a preservative. The pH is adjusted to between 6.8 and 7.2. Betamethasone sodium phosphate, a soluble ester, provides prompt activity, while betamethasone acetate is only slightly soluble and affords sustained activity. Such formulation is commercially available in the U.S. under the tradename Celestone Soluspan® (from Merck Sharp and Dohme Corp.) and as Betavet® (from Luitpold Pharmaceuticals, Inc.) for intra-articular use in horses is a sterile aqueous suspension of betamethasone acetate in betamethasone sodium phosphate injection. Celastone Soluspan is indicated for IM injection in allergic, dermatologic, rheumatic, and other conditions responsive to systemic corticosteroids, including bursitis; injection directly into the affected tissues in bursitis and associated inflammatory disorders of tendons such as tenosynovitis, and inflammatory disorders of muscle such as fibrosis and myositis; intra-articular and periarticular injection in rheumatoid arthritis and osteoarthritis; intralesional injection in various dermatologic conditions; and local injection in certain inflammatory and cystic disorders of the foot. Betamethasone sodium phosphate, a soluble ester, provides prompt activity, while betamethasone acetate is only slightly soluble and affords sustained activity. Betamethasone sodium phosphate injection (EQ 3 mg base/ml) was also available in the U.S. under the tradename Celastone (from Shering Corp.), but that product was discontinued.

Ataxia Pathophysiology

Ataxia describes a lack of muscle control during voluntary movements, such as walking or picking up objects. A sign of an underlying condition, ataxia can affect movement, speech, eye movement and swallowing. Persistent ataxia usually results from damage to the cerebellum—a part of the brain that controls muscle coordination. Many conditions can cause ataxia, including alcohol abuse, stroke, tumor, cerebral palsy and multiple sclerosis. An inherited defective gene can also cause ataxia. Treatment for ataxia depends on the cause. Adaptive devices, such as walkers or canes, might help maintain independence. Physical therapy, occupational therapy and speech therapy also might help.

Damage, degeneration or loss of nerve cells in the part of the brain that controls muscle coordination (cerebellum) results in ataxia. The cerebellum comprises two pingpong-ball-sized portions of folded tissue situated at the base of the brain near the brainstem. The right side of the cerebellum controls coordination on the right side of your body; the left side of the cerebellum controls coordination on the left.

Diseases that damage the spinal cord and peripheral nerves that connect the cerebellum to the muscles may also cause ataxia. The causes of ataxia include: (i) Head trauma (Damage to the brain or spinal cord from a blow to the head, such as might occur in a car accident, can cause sudden-onset ataxia, also known as acute cerebellar ataxia); (ii)

Stroke (When blood supply to a part of the brain is interrupted or severely reduced depriving brain tissue of oxygen and nutrients, brain cells die); (iii) Transient ischemic attack (TIA; Caused by a temporary decrease in blood supply to part of the brain. Most TIAs last only a few minutes. Loss of coordination and other signs and symptoms of a TIA are temporary); (iv) Cerebral palsy (This is a general term for a group of disorders caused by damage to a child's brain during early development—before, during or shortly after birth—that affects the child's ability to coordinate body movements); (v) Multiple sclerosis (MS, which is a chronic, potentially debilitating disease that affects the central nervous system; (vi) Chickenpox (Ataxia can be an uncommon complication of chickenpox and other viral infections. It may appear in the healing stages of the infection and last for days or weeks. Normally, the ataxia resolves over time); (vii) Paraneoplastic syndromes (These are rare, degenerative disorders triggered by the immune system's response to a cancerous tumor (neoplasm), most commonly from lung, ovarian, breast or lymphatic cancer. Ataxia may appear months or years before the cancer is diagnosed); (vii) Tumor (A growth on the brain, cancerous (malignant) or noncancerous (benign), can damage the cerebellum); (viii) Toxic reaction (Ataxia is a potential side effect of certain medications, especially barbiturates such as phenobarbital and sedatives such as benzodiazepines. Alcohol and drug intoxication; heavy metal poisoning such as from lead or mercury; and solvent poisoning such as from paint thinner, can also cause ataxia); (ix) Vitamin E or vitamin B-12 deficiency (Not getting enough vitamin E or vitamin B-12, because of the inability to absorb enough of the vitamin or other reasons can lead to ataxia).

For some adults who develop sporadic ataxia, no specific cause can be found. This is known as sporadic degenerative ataxia, which can take a number of forms, including multiple system atrophy, a progressive degenerative disorder.

Hereditary Ataxias

Some types of ataxia and some conditions that cause ataxia are hereditary. This is due to a birth defect in a certain gene that makes abnormal proteins. The abnormal proteins hamper the function of nerve cells, primarily in the cerebellum and spinal cord and cause them to degenerate. As the disease progresses, coordination problems worsen.

One can inherit genetic ataxia from either a dominant gene from one parent (autosomal dominant disorder) or a recessive gene from each parent (autosomal recessive disorder). In the latter case, it's possible that neither parent has the disorder (silent mutation), so there may be no obvious family history.

Different gene defects cause different types of ataxia, most of which are progressive. Each type causes poor coordination, but each has specific signs and symptoms.

Autosomal Dominant Ataxias

Spinocerebellar ataxias. Researchers have labeled more than 20 autosomal dominant ataxia genes, and the number is likely to continue to grow. Cerebellar ataxia and cerebellar degeneration are common to all types, but other signs and symptoms, as well as age of onset, differ depending on the specific gene mutation.

Episodic ataxia. There are seven recognized types of ataxia that are episodic rather than progressive—EA1 through EA7. EA1 and EA2 are the most common. EA1 involves brief ataxic episodes that may last seconds or minutes. The episodes are triggered by stress, being startled or sudden movement, and often are associated with muscle twitching. EA2 involves longer episodes, usually lasting from 30 minutes to six hours, that also are triggered by stress. With this type of ataxia, you may experience dizziness (vertigo), fatigue and muscle weakness during your episodes. In some cases of episodic ataxia, symptoms resolve in later life. Episodic ataxia doesn't shorten life span, and symptoms may respond to medication.

Autosomal Recessive Ataxias

Friedreich's ataxia. This, the most common hereditary ataxia, involves damage to your cerebellum, spinal cord and peripheral nerves. Peripheral nerves carry signals from your brain and spinal cord to your muscles. In most cases, signs and symptoms appear before the age of 25. The rate of disease progression varies. The first indication generally is difficulty walking (gait ataxia). The condition typically progresses to the arms and trunk. Muscles weaken and waste away over time, causing deformities, particularly in your feet, lower legs and hands. Other signs and symptoms that may develop as the disease progresses include slow, slurred speech (dysarthria); fatigue; rapid, involuntary eye movements (nystagmus); spinal curvature (scoliosis); hearing loss; and heart disease, including heart enlargement (cardiomyopathy) and heart failure.

Yet another related disease is Ataxia-telangiectasia (AT). The disease causes immune system breakdown (immunodeficiency disease), which increases susceptibility to other diseases. It affects various organs. AT is a rare genetic progressive autosomal recessive neurodegenerative disorder that affects children, with the hallmark symptoms of cerebellar ataxia and other motor dysfunction, and dilated blood vessels (telangiectasia) that occur in the sclera of the eyes. AT is caused by mutations in the ATM (ataxia telangiectasia mutated) gene, which is responsible for modulating cellular response to stress, including breaks in the double strands of DNA. Telangiectasias are tiny red "spider" veins that may appear in the corners of the child's eyes or on the ears and cheeks. Although characteristic of the disease, some children may not develop telangiectasias. Children begin to experience balance and coordination problems when they begin to walk (toddler age), and ultimately become wheelchair bound in their second decade of life. In pre-adolescence (age 5-8), patients experience oculomotor apraxia, dysarthria, and dysphagia. They also often develop compromised immune systems, and are at increased risk of developing respiratory tract infections and cancer (typically lymphomas and leukemia). Delayed motor skill development, poor balance and slurred speech are typically the first indications of the disease. Recurrent sinus and respiratory infections are common. AT is diagnosed through a combination of clinical assessment (especially neurologic and oculomotor deficits), laboratory analysis, and genetic testing. There is no known treatment to slow disease progression, and treatments that are used are strictly aimed at symptoms (e.g. physical, occupational or speech therapy for neurologic issues), or conditions secondary to the disease (e.g. antibiotics for lung infections, chemotherapy for cancer, etc.). Patients typically die by age 25 from complications of lung disease or cancer.

Patients with AT often develop lymphoid malignancies, and the treatmentregimens for these malignancies usually include glucocorticoids. The parents of patients with AT very quickly noted that the neurological symptoms associated with AT diminish, sometimes dramatically, during treatment with glucocorticoids (Gatti, 2009). This led to attempts to focus on the use of these drugs for long-term treatment of neurological problems.

Buoni et al (Betamethasone and improvement of neurological symptoms in ataxia telangiectasia. Arch Neurol 2006; 63: 1469-82) observed improvements in the neurological symptoms of a 3-year-old boy with the classic hallmarks, and a proven molecular diagnosis of AT within 2-3 days of administration of betamethasone (0.1 mg/kg/day). After 4 weeks of treatment, the improvement was dramatic: the disturbance of stance and gait was clearly reduced, the control of the head and neck and of skilled movements had increased, and the neurological improvement was so great that the child was able to go up and down stairs. The adverse effects observed were mainly an increase in appetite and body weight (from 15.5 kg to 19.0 kg at 4 weeks), associated with a change in phenotypic appearance (moon face). No beneficial effect was obtained when, in an attempt to perform long-term treatment, betamethasone was replaced after 4 weeks with methylprednisolone (2 mg/kg/day). Six months later, without therapy, the child continued to experience severe signs of central nervous system (CNS) impairment.

Broccoletti et al (Steroid-induced improvement of neurological signs in ataxia-telangiectasia patients. Eur J Neurol 2008; 15: 223-8) administered betamethasone (0.1 mg/kg/day) for 10 days to six consecutive patients (5-30 y). The neurological evaluation was performed through the Scale for the Assessment and Rating of Ataxia (SARA). Overall, five of the six patients exhibited a clear amelioration of the neurological performances. In two patients, a slight amelioration persisted 7 days after the therapy withdrawal, while in the other patients the score reached approximately the pre-treatment value at the end of the therapy. Twenty-eight of the 46 evaluated neurological items (60%) improved during therapy. The speech disturbance, finger chase and nose-finger test showed the more significant improvement. The clinical amelioration was inversely correlated with the level of cerebellum atrophy, as revealed by the magnetic resonance. Following on from this study, Broccoletti et al (Efficacy of very-low-dose betamethasone on neurological symptoms in ataxia-telangiectasia. Eur J Neurol 2011; 18:564-70) attempted to evaluate the minimum therapeutically effective dosage of betamethasone on neurological symptoms of AT. Six patients with AT (8-19 y), who had previously responded to a higher dose of betamethasone (0.1 mg/kg/day), received two 20-day cycles of oral betamethasone (0.01 and 0.03 mg/kg/day), each followed by a 20-day washout period. SARA scores significantly improved in all patients at the dosage of 0.03 mg/kg/day. Moreover, the effect was still appreciable at a dosage as low as 0.01 mg/kg/day, thus indicating the possibility of a significant reduction of side effects related to steroid therapy.

The evidence to date indicates that glucocorticoids in general exert their remarkable effects through both genomic and nongenomic mechanisms (Stahn, et al., Molecular mechanisms of glucocorticoid action and selective glucocorticoid receptor agonists. Mol Cell Endocrinol 2007; 275: 71-78; Bruscoli et al., Genomic and non-genomic effects of different glucocorticoids on mouse thymocyte apoptosis. Eur J Pharmacol 2006; 529: 63-70). The mechanism by which glucocorticoids, and betamethasone in particular, can alleviate the neurological symptoms associated with AT is not clear and is the subject of much speculation. It has been suggested that betamethasone could interact with specific receptor proteins in target tissues that regulate the expression of corticosteroid-responsive genes, prevent or suppress inflammation, enhance antioxidative pathways, enhance glucocorticoid receptors, or modulate synaptic plasticity (Buoni, 2006; Gatti et al. A proposed bailout for A-T patients? Eur J Neurol 2009; 16(6): 653-655; Zannolli et al., A randomized trial of oral betamethasone to reduce ataxia symptoms in Ataxia Telangiectasia. Mov Dis 2012; 27: 1312-16; Giardino et al., Betamethasone therapy in ataxia telangiectasia: unraveling the rationale of this serendipitous observation on the basis of the pathogenesis. European Journal of Neurology 2013, 20: 740-747). In a working theory of biochemical relationships in AT, Knittweis suggested that reduced levels of glutathione (GSH) may further alter differentiation of AT cells (Knittweis et al., An ataxia telangiectasia model: Inefficient cell differentiation and possible reversal by serine protease inhibitors, tumor necrosis factor inhibitors, dexamethasone, and glutathione enhancers. Medical Hypotheses. 1998; 51(1):53-57). In an attempt to define the underlying biochemical mechanism behind the improvement observed in AT patients receiving short-term betamethasone therapy, Russo et al (In ataxia-teleangiectasia betamethasone response is inversely correlated to cerebellar atrophy and directly to antioxidative capacity. Eur J Neurol 2009; 16: 755-9) evaluated intracellular GSH levels, lipid peroxidation levels and reactive oxygen species (ROS) production in six AT patients (5-29 y) treated with oral betamethasone (0.1 mg/kg/day) for 10 days, and compared those parameters with the improvement of cerebellar functions expressed as delta (D) of the SARA score. They observed an inverse correlation between D SARA and the severity of cerebellar atrophy and between the latter and basal GSH values. Four of the five patients with the highest D SARA also had the highest GSH values. Moreover, even though basal ROS values were comparable in patients and controls, in the only patient studied at different time-points of therapy, a remarkable reduction in ROS levels was documented. These results led Russo et al to suggest that antioxidative mechanisms play a role in favoring the improvement of cerebellar functions observed in AT patients receiving short-term betamethasone therapy.

In order to clarify whether the improvement is an epiphenomenon related to peripheral effect of the drug or rather an effect of the drug on the CNS performance activity, the same group set out to assess whether or not the motor performance changes observed with betamethasone were associated with functional magnetic resonance imaging (fMRI) modifications. SARA scores were once more evaluated in six AT patients who received a 10-day cycle of oral betamethasone at 0.03 mg/kg/day (Quarantelli et al, Steroid treatment in ataxia-telangiectasia induces alterations of functional magnetic resonance imaging during pronosupination task. Eur J Paediatr Neurol. 2013; 17 (2):135-140). The voxel-based comparison showed a remarkable increase in the number of activated voxels within the motor cortex under the on-therapy condition as compared with the cortical activity under baseline condition in the 2 patients who completed the study protocol, thus suggesting that steroid treatment could improve motor performance facilitating cortical compensatory mechanisms in AT patients.

In a multicenter, double-blind, randomized, placebo-controlled crossover trial, Zannolli et al studied the effect of betamethasone on the reduction of ataxia symptoms in 13 children (2-8 y) with AT (Zannolli et al., A randomized trial of oral betamethasone to reduce ataxia symptoms in Ataxia Telangiectasia. Mov Dis 2012; 27: 1312-16). Patients were randomly assigned to first receive either betamethasone or placebo at a dose of 0.1 mg/kg/day for 30 days: at full dose for the first 10 days, at a tapered dose on days 11-20 (i.e., for 4 days, 0.075 mg/kg/day; for 4 days, 0.050 mg/kg/day; and for 2 days, 0.025 mg/kg/day); and at full dose for the last 10 days (the full dose was tapered in the middle of the treatment phase to reduce risk from potential functional suppression of the hypothalamus-hypophysis-adrenal axis). Each phase of the trial was followed by a washout period of 30 days. The primary outcome measure was the reduction in ataxia symptoms as assessed by the International Cooperative Ataxia Rating Scale (ICARS). Betamethasone reduced the ICARS total score by a median of 13 points in the intent-to-treat (ITT) population and 16 points in the per-protocol (PP) population (i.e., median percent decreases of ataxia symptoms of 28% and 31%, respectively). In the ITT population, significant differences were observed in the posture and gait disturbance (p=0.02), kinetic function (p=0.02), and speech disorders ICARS subscales (p=0.02), but not in the oculomotor disorders subscale (p>0.05). Similar results were found in the PP population. Adverse events in the trial were minimal, with no compulsory withdrawals and only minor side effects that did not require medical intervention. Small increases in body weight were observed in 12 patients on betamethasone and in 4 patients on placebo. Moon face was present in 8 patients on betamethasone.

The effect of the betamethasone-related glucocorticosteroid, dexamethasone, on the neurological symptoms of AT has also been investigated in a Phase-2 study. Twenty two patients (mean age 11.2±3.5) with a confirmed diagnosis of AT and a preserved or partially supported gait received a monthly infusion of autologous erythrocyte-encapsulated dexamethasone (EryDex) for 6 months (Chessa et al, Intra-Erythrocyte Infusion of Dexamethasone Reduces Neurological Symptoms in Ataxia Teleangiectasia Patients: Results of a Phase 2 Trial. Orphanet Journal of Rare Diseases 2014; 9(5): 1-8). An improvement in ICARS was detected in the ITT population (n=22; p=0.02) as well as in PP population (n=18; p=0.01). When compared to baseline, a significant improvement were also found in the Vineland Adaptive Behavior Scales (VABS; p<0.0001, ITT) with statistically significant increases at 3 and 6 months (p<0.0001). After the end of the first trial, 4 patients continued to be treated with monthly EryDex infusions for an additional 24 months, and their clinical outcome was compared with that of 7 age-matched patients who stopped the treatment after the first 6 infusions (Leuzzi et al., Positive effect of erythrocyte-delivered dexamethasone in ataxia-telangiectasia. Neurol Neuroimmunol Neuroinflamm 2015; 2(3): e98, 1-4). Patients in the extended study experienced a continuous neurologic improvement with respect to their pretreatment status, whereas controls showed a progressive neurologic deterioration (according to the natural history of the disease) after the discontinuation of the treatment. None of the side effects usually associated with the chronic administration of corticosteroids were observed during the entire trial. This same group demonstrated a short direct repeat-mediated noncanonical splicing event induced by dexamethasone, which leads to the skipping of mutations upstream of nucleotide residue 8450 of ATM coding sequence (Menotta et al., Dexamethasone Partially Rescues Ataxia Telangiectasia-mutated (ATM) Deficiency in Ataxia Telangiectasia by Promoting a Shortened Protein Variant Retaining Kinase Activity. J Biol Chem. 2012; 287(49): 41352-41363). The resulting transcript provides an alternative ORF translated in a new ATM variant with the complete kinase domain. This miniATM variant was also highlighted in lymphoblastoid cell lines from AT patients and was shown to be likely active. Menotta et al concluded that induction of a truncated protein retaining kinase activity could represent one of the mechanisms by which the drug acts in treated AT patients.

The betamethasone studies have highlighted that during the clinical course of the disease there is a phase when neurological impairment may be rescued to some extent (Giardino et al., Betamethasone therapy in ataxia telangiectasia: unraveling the rationale of this serendipitous observation on the basis of the pathogenesis. European Journal of Neurology 2013; 20: 740-747).

Another related disease is congenital cerebellar ataxia. This type of ataxia results from damage to the cerebellum that is present at birth.

Yet another related disease is Wilson's disease. People with this condition accumulate copper in their brains, livers and other organs, which can cause neurological problems, including ataxia.

There is no specific treatment for ataxia. In some cases, treating the underlying cause resolves the ataxia. In other cases, such as ataxia that results from chickenpox or other viral infection, it's likely to resolve on its own over time.

SUMMARY OF THE INVENTION

It is an object of the invention to provide an ambient temperature stable oral solution of a glucocorticoid steroid that can be administered as a spray or as an oral solution.

It is an object of the invention to provide a pharmaceutically acceptable formulation of a glucocorticoid.

It is a further object of the invention to provide a pharmaceutically acceptable formulation of a glucocorticoid that can be administered orally, e.g., as an oral spray, for the treatment of neurological diseases.

In furtherance of the above objectives and others, the invention is directed in part to an oral spray formulation of glucocorticoid steroid for treating neurological disorders.

It is a further object of the present invention to oral solution and/or oral spray form of betamethasone.

It is a further object of the invention to provide an oral liquid formulation of betamethasone that is easier for a human patient suffering from a neurological disorder (such as AT) to swallow.

It is a further object of the invention to provide an oral solution and/or oral spray form of betamethasone for the treatment of patients suffering from ataxia, e.g., ataxia telangiectasia.

The above objects and others are provided by the present invention, which relates in part to a stable liquid glucocorticoid formulation comprising a glucocorticoid consisting of (i) a disodium salt of a glucocorticoid selected from the group consisting of betamethasone, dexamethasone, prednisolone, methylprednisolone, hydrocortisone and triamcinolone, and mixtures of any of the foregoing and (ii) less than 11% of a glucocorticoid base selected from (i) in its base form (i.e., whichever glucocorticoid(s) is selected from the group consisting of betamethasone, dexamethasone, prednisolone, methylprednisolone, hydrocortisone, triamcinolone, and mixtures of any of the foregoing), in a pharmaceutically acceptable aqueous solvent (e.g, water). In certain embodiments, the formulation further optionally comprises a preservative, a buffering and/or pH-modifying agent, a sweetening agent and other optional pharmaceutical excipients. In certain preferred embodiments, the liquid formulation is clear and is without precipitate (i.e., does not include particulate matter such as precipitate of glucocorticoid). In certain embodiments, the liquid formulation does not include a significant amount of precipitate (e.g., contains less than about 11% and most preferably less than about 10% glucocorticoid in its base form). In certain preferred embodiments, the pH of the liquid formulation is from about pH 2 to about pH 8. In certain preferred embodiments, the liquid formulation is an oral spray formulation which contains the disodium phosphate salt of the glucocorticoid in a concentration from about 0.25 to about 12 mg/ml, and provides a therapeutically effective dose in from about 1 to about 3 sprays. In certain preferred embodiments, the concentration of glucocorticoid in the aqueous liquid formulation is from about 2.35 mg/ml to about 12 mg/ml, based on the glucocorticoid in its disodium salt form. In certain further preferred embodiments, the concentration of glucocorticoid in the aqueous liquid formulation is from about 3.57 mg/ml to about 8.93 mg/ml, and in other embodiments from about 7.14 mg/ml to about 8.93 mg/ml, based on the glucocorticoid in its base form. In certain preferred embodiments, the glucocorticoid consists of betamethasone. In certain embodiments, the liquid formulation comprises a plurality of spray droplets, each spray providing a liquid volume from about 0.040 ml to about 0.350 ml, and most preferably in certain embodiments a liquid volume of about 0.14 ml. In certain preferred embodiments, each spray of the liquid formulation provides a glucocorticoid dose from about 0.33 mg to about 1.65 mg (based on 0.14 ml spray volume). In certain preferred embodiments, at least 90% of the liquid droplet size is more than 10 microns in order to prevent the inhalation of glucocorticoid into the lungs. Preferably, the liquid formulation is clear and without precipitate for at least about 24 months when stored at a temperature from about 2° C. to about 25° C. The concentrations provided above will change slightly depending on the molecular weight of the respective glucocorticoid base. The concentration ratio between the base and disodium phosphate for the glucocorticoids mentioned above varies between 1.28-1.34. The concentrations set forth above are based on betamethasone. In certain preferred embodiments, the glucocorticoid consists of betamethasone.

In certain preferred embodiments, the formulation comprises a supersaturated concentration of the drug (glucocorticoid). In certain preferred embodiments, the disodium salt of the glucocorticoid is a disodium phosphate salt. In certain preferred embodiments, the liquid formulation further includes (optional) pharmaceutically acceptable excipients, including but not limited to buffering or pH-adjusting agents, preservatives, and (water-soluble) sweeteners. In certain embodiments, the stable oral spray formulation is stored at room temperature. In other embodiments, the stable oral spray formulation is stored at a temperature from about 2° C. to about 25° C. In certain preferred embodiments, the formulation is stored at a temperature from about 2° C. to about 8° C. In certain preferred embodiments, the stable oral spray formulation has a shelf life of at least about 24 months, and in certain embodiments up to about 36 months.

The invention is also directed in part to a stable oral spray formulation of betamethasone, consisting of a (solubilized) disodium salt of betamethasone in an aqueous solvent in a concentration from about 0.25 mg/ml to about 12 mg/ml, and in further embodiments from about 2.357 mg/ml to about 9.429 mg/ml, the oral spray formulation containing less than 10% betamethasone in base form. In preferred embodiments, the stable oral spray formulation comprises a unit dose of liquid droplets of the formulation, wherein each spray comprises a liquid volume of from about 0.040 ml to about 0.350 ml, and preferably about 0.14 ml. In certain preferred embodiments, the disodium salt of betamethasone is the disodium phosphate betamethasone salt. In certain preferred embodiments, not more than about 10% of the liquid droplets have a diameter less than 10 microns. The liquid droplets preferably have a size distribution of from about 5 microns to about 500 microns. In certain preferred embodiments, the solvent does not include any organic solvent(s). In certain preferred embodiments, the concentration of betamethasone in the aqueous liquid formulation is from about 2.35 mg/ml to about 12 mg/ml, based on the glucocorticoid in its disodium salt form. In certain further preferred embodiments, the concentration of betamethasone in the aqueous liquid formulation is from about 3.57 mg/ml to about 8.93 mg/ml, and in other embodiments from about 7.14 mg/ml to about 8.93 mg/ml, based on betamethasone in its base form. In certain preferred embodiments, each spray of the stable oral spray formulation contains the sodium salt of betamethasone in a concentration from about 0.33 mg/0.14 ml to about 1.32 mg/0.14 ml. In other embodiments, the stable oral spray formulation is supersaturated, i.e., contains the disodium phosphate salt of betamethasone in solution in an amount of about 1.65 mg dissolved in 0.14 ml (about 11.786 or 12 mg/ml). In certain preferred embodiments, the liquid formulation is clear and is without precipitate (i.e., does not include particulate matter such as precipitate of betamethasone base). In other embodiments, the liquid formulation does not include a significant amount of precipitate (e.g., contains about 11% or less, and most preferably less than about 10% betamethasone base). In certain preferred embodiments, the pH of the liquid formulation is from about pH 2 to about pH 8. In certain preferred embodiments, the concentration of the stable oral spray formulation is from about 2.35 to about 11.79 mg/ml (e.g., from about 1.78 mg/ml to about 8.93 mg/ml EQ to betamethasone base). In certain embodiments, the stable oral spray formulation is stored at room temperature. In other embodiments, the stable oral spray formulation is stored at a temperature from about 2° C. to about 25° C. In certain preferred embodiments, the formulation is stored at a temperature from about 2° C. to about 8° C. In certain preferred embodiments, the stable oral spray formulation has a shelf life of at least about 24 months, and in certain embodiments up to about 36 months.

In further embodiments, the invention relates in part to an oral formulation comprising a glucocorticoid steroid, a pharmaceutically acceptable buffering agent in an amount sufficient to provide the formulation with a pH from about 2 to about 8, in a pharmaceutically acceptable solvent. Optionally, the formulation further comprises effective amounts of a pharmaceutically acceptable preservative, a pharmaceutically acceptable sweetener, and other pharmaceutical excipients. In certain preferred embodiments, the invention relates in part to an oral spray formulation, comprising betamethasone sodium phosphate in a pharmaceutically acceptable solvent for oral administration to humans, the concentration of the betamethasone in solution being from about 0.25 mg to about 12 mg per mL of the oral spray formulation, the oral spray formulation further optionally comprising a preservative, a buffering agent, a sweetening agent and other optional pharmaceutical excipients. In certain embodiments, the concentration of the betamethasone in solution is from about 1.78 to about 8.93 mg/ml, or from about 3.57 to about 8.93 mg/ml. or from about 7.14 to about 8.93 mg/ml based on the betamethasone in its base form. In certain embodiments, the stable oral spray formulation is stored at room temperature. In other embodiments, the stable oral spray formulation is stored at a temperature from about 2° C. to about 25° C. In certain preferred embodiments, the formulation is stored at a temperature from about 2° C. to about 8° C. In certain preferred embodiments, the stable oral spray formulation has a shelf life of at least about 24 months, and in certain embodiments up to about 36 months.

The invention is further directed in part to a stable oral spray formulation of betamethasone, consisting of a (solubilized) disodium phosphate salt of betamethasone in an aqueous solvent in a concentration from about 0.33 mg/spray to about 10 mg/spray, wherein each spray is about 0.14 ml, the stable oral spray formulation being maintained during storage at a temperature from about 2° C. to about 8° C., and the formulation being stable over its entire shelf life of at least 24 months. In certain preferred embodiments, not more than about 10% of the liquid droplets have a diameter less than 10 microns. The liquid droplets preferably have a size distribution of from about 5 microns to about 500 microns. In certain preferred embodiments, the solvent does not include any organic solvent(s). In certain preferred embodiments, the concentration of betamethasone in the aqueous liquid formulation is from about up to about 71.4 mg/ml based on the glucocorticoid in its disodium salt form. In certain further preferred embodiments, the concentration of betamethasone in the aqueous liquid formulation is up to about 54.09 mg/ml based on betamethasone in its base form. In other preferred embodiments, the stable oral spray formulation is supersaturated. In further embodiments, the stable oral spray formulation contains the disodium phosphate salt of betamethasone in solution in an amount of up to about 10 mg dissolved in 0.14 ml (up to about 71.4). In certain preferred embodiments, the liquid formulation is clear and is without precipitate (i.e., does not include particulate matter such as precipitate of betamethasone base). In other embodiments, the liquid formulation does not include a significant amount of precipitate (e.g., contains about 11% or less betamethasone base, and most preferably less than about 10% betamethasone base). In certain preferred embodiments, the pH of the liquid formulation is from about pH 2 to about pH 8. In certain embodiments, the stable oral spray formulation is a supersaturated solution, meaning that the formulation will remain as a clear solution during storage up to the shelf life of drug product (e.g., at least about 24 months, and up to about 36 months in certain embodiments. The stable oral spray formulation solution reaches a supersaturated state at the end of product shelf life when stored at room temperature.

The oral formulations of the invention can be in the form of syrup, an aqueous solution, suspension, or oral drops. Alternatively, the oral formulation can be in the form of a reconstituted powder in an aqueous solution that contains a buffer to regulate the pH of the solution.

In certain preferred embodiments, the glucocorticoid is betamethasone and/or dexamethasone and/or prednisolone, in their base form or pharmaceutical acceptable salts, most preferably in the form of their (di)sodium phosphate salts.

In certain preferred embodiments, the formulation is a sprayable formulation, preferably a metered dose oral spray which can be sprayed in the oral cavity of a human patient, e.g., over the tongue. In some embodiments, delivered spray is a plume or a stream over the tongue.

The present invention is also directed to a method for treating and/or preventing neurological disorder in a subject (e.g., mammal, preferably human) who has difficulty in swallowing by administering to said patient a pharmaceutically effective amount of glucocorticoid steroid, in an oral liquid formulation that can be sprayed over the tongue.

In certain embodiments, the invention is directed to a method of treating a neurological disorder in a human patient comprising orally administering a stable oral liquid formulation of a solubilized disodium salt of a glucocorticoid consisting of (i) a disodium salt of a glucocorticoid selected from the group consisting of betamethasone, dexamethasone, prednisolone, methylprednisolone, hydrocortisone and triamcinolone, and mixtures of any of the foregoing and (ii) about 11% or less of a glucocorticoid base selected from the group consisting of betamethasone, dexamethasone, prednisolone, methylprednisolone, hydrocortisone, triamcinolone, and mixtures of any of the foregoing, by spraying a unit dose of the glucocorticoid over the tongue of the human patient, the stable oral liquid formulation having a concentration of the disodium salt of the glucocorticoid from about 0.25 mg/ml to about 12 mg/ml, wherein each spray has a liquid volume from about 0.040 to about 0.350 ml and the unit dose is delivered in from about 1 to about 20 sprays, and in certain preferred embodiments from about 1 to about 5 sprays. In certain preferred embodiments, the concentration of the solubilized glucocorticoid is preferably from about 0.33 mg/0.14 ml to about 1.32 mg/0.14 ml. In other preferred embodiments, the stable oral spray formulation is supersaturated. Supersaturated solution for the purposes of the present invention means that the formulation will remains in the clear solution during storage at 25° C. up to the shelf life of drug product (e.g., at least 24 months, or up to about 36 months). In the present invented formulation, the aqueous liquid (solution) reaches its supersaturated state at the end of product shelf life when stored at room temperature. In certain preferred embodiments, the stable oral liquid formulation further comprises a pharmaceutically acceptable non-organic solvent, such as water. In certain preferred embodiments, the liquid formulation is clear and is without precipitate (i.e., does not include particulate matter such as precipitate of glucocorticoid base). In preferred embodiments, the liquid formulation does not include a significant amount of precipitate (e.g., contains less than about 11% and preferably less than about 10% glucocorticoid base). In certain preferred embodiments, the glucocorticoid salt consists of the disodium phosphate salt of betamethasone. In certain preferred embodiments, at least 90% of the liquid droplet size is more than 10 microns in order to prevent the inhalation of glucocorticoid into the lungs. In certain preferred embodiments, the liquid droplets preferably have a size distribution of from about 5 microns to about 500 microns. In certain embodiments, the neurological disorder is ataxia. In certain preferred embodiments, the neurological disorder is ataxia telangiectasia. In certain embodiments, the human patient is a pediatric patient. In preferred embodiments, the glucocorticoid is betamethasone.

The invention is also directed in part to a method for treating a neurological disorder with an oral glucocorticoid, comprising orally administering to a human patient a stable oral liquid formulation of a solubilized disodium salt of a glucocorticoid consisting of (i) a disodium salt of a glucocorticoid selected from the group consisting of betamethasone, dexamethasone, prednisolone, methylprednisolone, hydrocortisone and triamcinolone, and mixtures of any of the foregoing and (ii) less than 11% of the corresponding base form of the glucocorticoid, in water, by spraying a unit dose of the glucocorticoid over the tongue of the human patient, the stable oral liquid formulation having a concentration of the disodium salt of the glucocorticoid from about 0.25 mg/ml to about 12 mg/ml, wherein each spray has a liquid volume from about 0.040 to about 0.350 ml and the unit dose is delivered in from about 1 to about 20 sprays from a mechanical spray device, and the stable oral liquid spray formulation is clear and without precipitate. In preferred embodiments, the glucocorticoid is betamethasone.

The invention is also directed in part to a method for treating a neurological disorder, comprising orally administering to a human patient a stable oral liquid spray formulation of a solubilized disodium phosphate salt of betamethasone in water by spraying a unit dose of the solubilized disodium phosphate salt of betamethasone into the oral cavity of a human patient, wherein the unit dose comprises from 1 to about 7 sprays of the stable oral liquid formulation and the concentration of the disodium phosphate salt of betamethasone in the formulation is from about 3.57 mg/ml to about 8.93 mg/ml EQ to betamethasone base and the stable oral liquid spray formulation is clear and without precipitate.

The invention is also directed in part to a method of treating a human patient who has difficulty swallowing with a glucocorticoid, comprising orally administering to the human patient a stable oral liquid formulation of a solubilized disodium salt of a glucocorticoid consisting of (i) a disodium salt of a glucocorticoid selected from the group consisting of betamethasone, dexamethasone, prednisolone, methylprednisolone, hydrocortisone and triamcinolone, and mixtures of any of the foregoing, in water, by spraying a unit dose of the glucocorticoid over the tongue of the human patient, the stable oral liquid formulation having a concentration of the disodium salt of the glucocorticoid from about 0.25 mg/ml to about 12 mg/ml, wherein each spray has a liquid volume from about 0.040 to about 0.350 ml and the unit dose is delivered in from about 1 to about 20 sprays from a mechanical spray device, and the stable oral liquid spray formulation is clear and without precipitate. In certain preferred embodiments, each spray has a liquid volume of about 0.14 ml. In certain preferred embodiments, the concentration of the disodium phosphate salt of glucocorticoid in the formulation is from about 3.57 mg/ml to about 8.93 mg/ml EQ to glucocorticoid base and the stable oral liquid spray formulation is clear and without precipitate. In preferred embodiments, the glucocorticoid is betamethasone.

In certain preferred embodiments, the oral spray of the glucocorticoid (e.g., betamethasone) is delivered in 1, 2, 3, 4, 5, 6, 7, 8, 9, 10, 11, 12, 13, 14, 15, 16, 17, 18 19 or 20 sprays. In certain preferred embodiments, a unit dose of the oral spray is delivered in from about 1 to about 7 sprays (e.g., of a mechanically actuated oral spray device).

In certain preferred embodiments, the concentration of disodium salt of the glucocorticoid in the oral spray formulation is about 0.25 mg/0.14 ml, 0.26 mg/0.14 ml, 0.27 mg/0.14 ml, 0.28 mg/0.14 ml, 0.29 mg/0.14 ml, 0.30 mg/0.14 ml, 0.31 mg/0.14 ml, 0.32 mg/0.14 ml, 0.33 mg/0.14 ml, 0.34 mg/0.14 ml or 0.35 mg/0.14 ml, 0.36 mg/0.14 ml, 0.37 mg/0.14 ml, 0.38 mg/0.14 ml, 0.39 mg/0.14 ml, 0.40 mg/0.14 ml, 0.41 mg/0.14 ml, 0.42 mg/0.14 ml, 0.43 mg/0.14 ml, 0.44 mg/0.14 ml, 0.45 mg/0.14 ml, 0.46 mg/0.14 ml, 0.47 mg/0.14 ml, 0.48 mg/0.14 ml, 0.49 mg/0.14 ml, 0.50 mg/0.14 ml, 0.51 mg/0.14 ml, 0.52 mg/0.14 ml, 0.53 mg/0.14 ml, 0.54 mg/0.14 ml, 0.55 mg/0.14 ml, 0.56 mg/0.14 ml, 0.57 mg/0.14 ml, 0.58 mg/0.14 ml, 0.59 mg/0.14 ml, 0.60 mg/0.14 ml, 0.61 mg/0.14 ml, 0.62 mg/0.14 ml, 0.63 mg/0.14 ml, 0.64 mg/0.14 ml, 0.65 mg/0.14 ml, 0.66 mg/0.14 ml, 0.67 mg/0.14 ml, 0.68 mg/0.14 ml, 0.69 mg/0.14 ml, 0.70 mg/0.14 ml, 0.71 mg/0.14 ml, 0.72 mg/0.14 ml, 0.73 mg/0.14 ml, 0.74 mg/0.14 ml, 0.75 mg/0.14 ml, 0.76 mg/0.14 ml, 0.77 mg/0.14 ml, 0.78 mg/0.14 ml, 0.79 mg/0.14 ml, 0.80 mg/0.14 ml, 0.81 mg/0.14 ml, 0.82 mg/0.14 ml, 0.83 mg/0.14 ml, 0.84 mg/0.14 ml, 0.85 mg/0.14 ml, 0.86 mg/0.14 ml, 0.87 mg/0.87 ml, 0.88 mg/0.14 ml, 0.89 mg/0.14 ml, 0.90 mg/0.14 ml, 0.91 mg/0.14 ml, 0.92 mg/0.14 ml, 0.93 mg/0.14 ml, 0.94 mg/0.14 ml, 0.95 mg/0.14 ml, 0.96 mg/0.14 m, 0.97 mg/0.14 ml, 0.98 mg/0.14 ml, 0.99 mg/0.14 ml, 1.00 mg/0.14 ml, 1.01 mg/0.14 ml, 1.02 mg/0.14 ml, 1.03 mg/0.14 ml, 1.04 mg/0.14 ml, 1.05 mg/0.14 ml, 1.06 mg/0.14 ml, 1.07 mg/0.14 ml, 1.08 mg/0.14 ml, 1.09 mg/0.14 ml, 1.10 mg/0.14 ml, 1.11 mg/0.14 ml, 1.12 mg/0.14 ml, 1.13 mg/0.14 ml, 1.14 mg/0.14 ml, 1.15 mg/0.14 ml, 1.16 mg/0.14 ml, 1.17 mg/0.14 ml, 1.18 mg/0.14 ml, 1.19 mg/0.14 ml, 1.20 mg/0.14 ml, 1.21 mg/0.14 ml, 1.22 mg/0.14 ml, 1.23 mg/0.14 ml, 1.24 mg/0.14 ml, 1.25 mg/0.14 ml, 1.26 mg/0.14 ml, 1.27 mg/0.14 ml, 1.28 mg/0.14 ml, 1.29 mg/0.14 ml, 1.30 mg/0.14 ml, 1.31 mg/0.14 ml, 1.32 mg/0.14 ml, 1.33 mg/0.14 ml, 1.34 mg/0.14 ml, 1.35 mg/0.14 ml, 1.36 mg/0.14 ml, 1.37 mg/0.14 ml, 1.38 mg/0.14 ml, 1.39 mg/0.14 ml, 1.40 mg/0.14 ml, 1.41 mg/0.14 ml, 1.42 mg/0.14 ml, 1.43 mg/0.14 ml, 1.44 mg/0.14 ml, 1.45 mg/0.14 ml, 1.46 mg/0.14 ml, 1.47 mg/0.14 ml, 1.48 mg/0.14 ml, 1.49 mg/0.14 ml, 1.50 mg/0.14 ml, 1.51 mg/0.14 ml, 1.52 mg/0.14 ml, 1.53 mg/0.14 ml, 1.54 mg/0.14 ml, 1.55 mg/0.14 ml, 1.56 mg/0.14 ml, 1.57 mg/0.14 ml, 1.58 mg/0.14 ml, 1.59 mg/0.14 ml, 1.60 mg/0.14 ml, 1.61 mg/0.14 ml, 1.62 mg/0.14 ml, 1.63 mg/0.14 ml, 1.64 mg/0.014 ml, 1.65 mg/0.14 ml, 1.66 mg/0.14 ml, 1.67 mg/0.14 ml, or 1.68 mg/0.14 ml.

The liquid pharmaceutical composition of this invention preferably contains a pharmaceutically effective amount of a soluble salt of a glucocorticoid steroid (e.g., a disodium salt of betamethasone and/or dexamethasone and/or hydrocortisone, and/or triamcinolone and/or prednisolone and/or methylprednisolone) in a pharmaceutically acceptable liquid carrier e.g. purified water, and a buffer, e.g. citrate, to maintain the pH at from about 2 to about 8 and preferably at a pH from about 3 to about 6. The formulation may also include an optional complexing agent, e.g. citrate or EDTA, to inhibit the precipitation of drug substance from the aqueous medium.

In certain preferred embodiments, the liquid formulation of the invention is an aqueous solution that contains a high concentration of sugar or sugar substitute (e.g., sorbitol) thus providing for a syrup, which can be flavored for marketing desirability. In certain preferred embodiments, the amount of sugar or sugar substitute is from about 5 to about 90%, by weight.

In other embodiments, the stable liquid formulation of the invention is an oral syrup or an oral suspension. In yet other embodiments, the liquid formulation of the invention is an injectable formulation, wherein the pharmaceutically acceptable solvent comprises water for injection.

Also provided is a pharmaceutical composition comprising a powder for reconstitution containing a pharmaceutically effective amount of glucocorticoid steroid in particular betamethasone and/or dexamethasone in a pharmaceutically acceptable dry (solid) excipient also in the presence of a buffer, e.g. citrate, and complexing agent, said powder capable of dissolving in water.

Also provided is a pharmaceutical composition comprising oral drops containing a pharmaceutically effective amount of glucocorticoid steroid in particular betamethasone and/or dexamethasone in a pharmaceutically acceptable excipient also in the presence of a buffer, e.g. citrate, and complexing agent, said drops capable of dissolving in water or a suitable solvent and that can be sprayed using a spray pump.

Also provided is a pharmaceutical composition comprising an oral spray over the tongue containing a pharmaceutically effective amount of glucocorticoid steroid in particular betamethasone and/or dexamethasone in a pharmaceutically acceptable excipient also in the presence of a buffer, e.g. citrate and/or complexing agent.

The invention is also directed in part to a method of treating a neurological disorder comprising administering the liquid formulation of the present invention to a subject (e.g., human patient). In certain preferred embodiments, the liquid formulation is sprayed into the oral cavity (e.g., over the tongue) of the patient in the form of liquid droplets. The liquid droplets preferably have a size distribution of from about 5 microns to about 500 microns.

The invention is further directed in part to a method for treating a neurological disorder, comprising preparing a non-propellant based betamethasone oral liquid spray formulation having a concentration of solubilized betamethasone from about 0.25 mg to about 1 mg per 0.14 mL of the oral spray formulation, storing the glucocorticoid formulation in a metered dose mechanical spray pump device, and administering a therapeutically effective dose of said glucocorticoid into the oral cavity of a patient in need thereof by spraying from about 1 to about 5 spray actuations of the mechanical spray pump, wherein each spray actuation delivers about 0.14 mL of the oral spray formulation. In certain preferred embodiments, the oral spray droplet size of 90% of the liquid particles (Dv(90)) is 131 µm±30.

The invention is further directed in part to a method of treating a neurological disorder in a human, comprising orally administering to a human patient in need thereof a therapeutically effective amount of a propellant-free oral betamethasone spray formulation having a concentration of solubilized betamethasone from about 0.25 mg to about 1 mg per 0.14 mL of the oral spray formulation. In certain preferred embodiments, the dose administered is from about 0.25 mg to about 4 mg over a 12 hour period.

In certain preferred embodiments of the invention, the dose of betamethasone is titrated until steady-state is achieved. In such embodiments, the dose of the oral betamethasone spray formulation during a titration phase is from about 0.01 to about 0.2 mg/kg patient body weight administered once over a 12 hour and or 24 hour period. This translates to a betamethasone dose from about 0.07 mg to about 28 mg total per day, based on an average adult weighing 70 kg (based on betamethasone base). In other embodiments, the betamethasone dose may be from about 0.07 mg to about 14 mg for once daily dosing (every 24 hours) and from about 0.14 mg to about 28 mg for twice-a-day dosing (every 12 hours), based on an average adult weighing 70 kg (based on betamethasone base). The titration period may be, e.g., from about 2 to about 4 weeks, until steady-state is achieved. The dose can be further titrated based on the individual patient response. The dose of the oral betamethasone spray formulation at steady-state in such embodiments is preferably from about 0.02 to about 0.1 mg/kg patient body weight administered once over a 12 hour and or 24 hour period.

The invention is further directed in part to a method of treating a human patient with an oral betamethasone formulation, comprising orally administering to a human patient in need thereof a therapeutically effective amount of a propellant-free oral betamethasone spray formulation having a concentration of solubilized betamethasone from about 0.25 mg to about 1 mg per 0.14 mL of the oral spray formulation.

The invention is further directed in part to a method of treating a neurological disorder in a human, comprising orally administering to a human patient in need thereof a therapeutically effective dose of a propellant-free oral betamethasone spray formulation contained in a metered dose mechanical spray pump device which provides liquid particles which have a Dv(90) of about 131 µm±30 when the device is actuated, wherein the therapeutically effective dose is administered in from 1 to about 10 actuations. In certain preferred embodiments, the concentration of solubilized betamethasone in the oral betamethasone spray formulation is from about 0.25 mg to about 1 mg per 0.14 mL, or to about 1.32 mg per 0.14 ml.

The invention is further directed in part to a method of treating a neurological disorder in a human, comprising orally administering to a human patient in need thereof a therapeutically effective amount of a propellant-free oral betamethasone spray formulation having a concentration of solubilized betamethasone from about 0.25 mg to about 1 mg per 0.14 mL of the oral spray formulation. In preferred embodiments, the dose administered is from about 0.25 mg to about 4 mg over a 12 hour period. In preferred embodiments, the dose of the oral betamethasone spray formulation during a titration phase is from about 0.01 to about 0.2 mg/kg patient body weight administered once over a 12 hour and or 24 hour period, and the dose of the oral betamethasone spray formulation at steady-state is from about 0.02 to about 0.1 mg/kg patient body weight administered once over a 12 hour and or 24 hour period. In certain preferred embodiments, the neurological condition is ataxia. In further embodiments, the neurological condition is Ataxia-telangiectasia (AT).

In certain embodiments, a therapeutically effective dose of a propellant-free oral betamethasone spray formulation contained in a metered dose mechanical spray pump device which provides liquid particles which have a Dv(90) of about 131 µm±30 when the device is actuated, wherein the therapeutically effective dose is administered in from 1 to about 10 actuations.

In certain embodiments, the oral spray formulation of the invention is lyophilized, and the method further comprises reconstituting the spray formulation from a dry state by admixing with a suitable solvent(s) prior to administration.

In preferred embodiments, the aqueous formulation of the present invention is stable for at least 6 months, preferably 12 months, more preferably 24 months, and even preferably 36 months at room temperature. Preferably, the conversion to betamethasone base during storage at about 25° C. should not be more than 15% of total betamethasone in the formulation, and even preferably not more than 10% of total betamethasone in the formulation.

In certain preferred embodiments, the oral spray formulation provides a maximum mean plasma concentration of betamethasone about 190 ng/ml in-vivo after an oral application of 0.1 mg/kg/day betamethasone.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein, the singular form "a", "an" and "the" include plural references unless the context clearly dictates otherwise. For example, the term "a compound" or "at least one compound" may include a plurality of compounds, including mixtures thereof.

As used herein, the term "unit dose" refers to physically discrete units suitable as unitary dosages for mammalian subjects, each unit containing as the active ingredient a predetermined quantity of the active agent (e.g., glucocorticoid steroid).

The term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to effect treatment for that disease.

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes neurological disorders.

For purposes of the present invention, all percentages described herein are "w/w" unless otherwise specified.

The term "comprising" is an inclusive term interpreted to mean containing, embracing, covering or including the elements listed following the term, but not excluding other unrecited elements. The terms "comprises", "comprising", "includes", "including", "having" and their conjugates mean "including but not limited to".

For purposes of the present disclosure, the term "consisting of" is considered to be a preferred embodiment of the term "comprising of". If hereinafter a group is defined to comprise at least a certain number of embodiments, this is also meant to encompass a group that preferably consists of these embodiments only. The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

DETAILED DESCRIPTION

Figure 1:
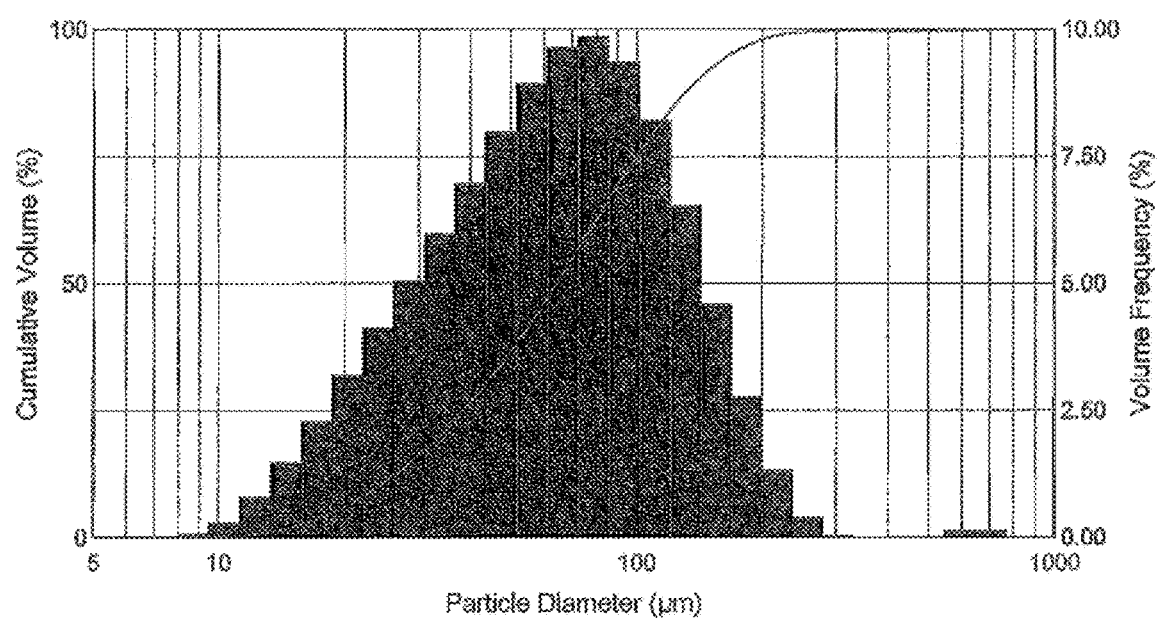
FIG. 1 is a graph depicting the average droplet size distribution plot of Example 1.

The invention will be described with reference to various specific and preferred embodiments and techniques, however, it should be understood that many variations and modifications can be made while remaining with the spirit and scope of the invention.

Corticosteroids such as betamethasone, dexamethasone, and prednisolone are anti-inflammatory drugs; they are often available as the corresponding 21-phosphate esters that are formulated into various dosage forms due to their much-enhanced solubility in an aqueous environment. Yet, the introduction of the phosphate group at the 21-hydroxyl of the steroid core structures might impart additional degradation pathways to the resulting hydrolysis and conversion to betamethasone base, which will precipitate out from the solution at higher temperature during storage. In the solid state it is only stable when stored in tightly closed container at a temperature from 2° C. to 8° C. For example, the stability of betamethasone sodium phosphate is very low in aqueous solution and strongly influenced by storage temperature.

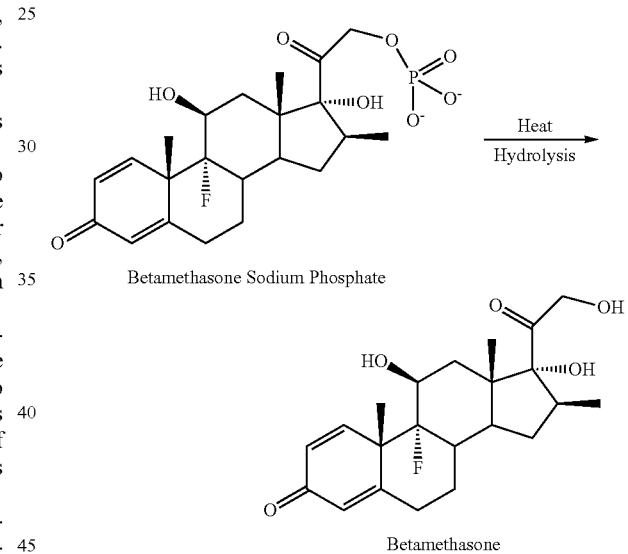

Betamethasone Sodium Phosphate

Betamethasone

The formula for betamethasone sodium phosphate is $C_{22}H_{28}FN_{a2}O_8P$ and it has a molecular weight of 516.41. Chemically, it is 9-Fluoro-11β,17,21-trihydroxy-16β-methylpregna-1,4-diene-3,20-dione 21-(disodium phosphate).

The aqueous formulation of the present invention is stable for at least 6 months, preferably 12 months, more preferably 24 months, and even preferably 36 months. "Aqueous formulation of the present invention is stable" means that after 6, 12, 24 or 36 months at a selected temperature (preferably at about 25° C.) the amount of the sodium salt (e.g., disodium phosphate salt) of the soluble glucocorticoid (e.g., betamethasone) present in the aqueous formulation of the present invention is reduced by a maximum of 10%, and preferably by a maximum of 8%, compared to the amount present initially after preparation of the aqueous formulation, preferably after filtration step if any. In preferred embodiments, the aqueous formulation of the present invention is stable for at least 24 months, and even preferably 36 months. The liquid formulation does not contain any precipitation (it is a clear solution).

The inventors observed that if more than 11% betamethasone base formed during the storage of disodium phosphate salt formulation at 25° C. (stability testing), betamethasone base precipitates out from the formulation because of poor aqueous solubility. This is not acceptable for a stable formulation. With respect to the aqueous (liquid) formulation of the present invention, the term "stable" means that the conversion of the disodium phosphate salt of the glucocorticoid(s) to glucocorticoid base (e.g., disodium phosphate salt of betamethasone to betamethasone base) during storage at about 25° C. should not be more than 11% of total betamethasone in the formulation, and more preferably not more than 10% of total betamethasone in the formulation. In certain embodiments, for example, the betamethasone base precipitates out in the oral spray formulation when it converts to more than 0.15 mg/0.14 ml (spray volume) (equivalent to 1.07 mg/ml).

In certain embodiments, the stability of the glucocorticoid (e.g., betamethasone) in the formulation can be improved by storing the formulation of the invention at temperature below 10° C., and in certain embodiments preferably between about 2° C. and about 8° C.

Oral solutions of glucocorticoid steroid, in the form of an oral spray, drop, syrup, an aqueous solution, or a reconstituted aqueous solution of a powder offer the advantages of ease of administration, increased compliance for patients who have difficulty swallowing solid oral dosage forms and/or large volumes of liquid formulation. An oral spray formulation also offers the additional advantage of minimizing storage space in nursing homes, pharmacies, hospitals and warehouses. These formulations have the advantage of permitting dose titration should this be desired based on the patient weight.

In the present invention, an oral spray can be prepared, for example, by adding the drug, buffering agent, preservatives and sweetening agent to the solvent while stirring the solution to ensure complete dissolution of the drug and excipients. Aqueous or hydro alcoholic solvents can be utilized for the liquid formulations of the invention. The formulations can be stored, e.g., in glass vials sealed tightly with a cap or spray pump.

In certain embodiments, the formulation of the invention is a multi-dose and or unit dose of a glucocorticoid (e.g., betamethasone) oral spray formulation, this formulation comprising liquid droplets of glucocorticoid, a pharmaceutically acceptable salt thereof, or derivative thereof; and a pharmaceutically acceptable solvent carrier. The liquid droplets preferably have a size distribution of from about 5 microns to about 500 microns.

Any pharmaceutically acceptable glucocorticoid in water-soluble form can be used in the formulations of the invention. Representative examples include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof. Betamethasone, dexamethasone, triamcinolone, prednisolone, methylprednisolone and hydrocortisone are preferred, and their disodium phosphate salts are especially preferred. A portion of the glucocorticoid(s) may be in base form, but it is preferred that the amount of glucocorticoid base is limited such that the base does not precipitate out of the solvent (e.g., water). In other embodiments, the glucocorticoid may be in the form of other (water-soluble) pharmaceutically acceptable salts or complexes.

In certain preferred embodiments, the liquid formulations of the invention include a pH modifying agent and/or a buffer in order to adjust the pH of the liquid to a pH from about 2 to about 8, and in certain preferred embodiments to a pH from about 3 to about 7. Examples of pharmaceutically acceptable pH modifying agents (e.g., alkalizing agents) alkalizing agents include but are not limited to NaOH, KOH, triethylamine, meglumine, L-Arginine, sodium bicarbonate, and mixtures of any of the foregoing. Additional examples of pH modifying agents include, for example, but are not limited to, one or more adipic acids, glycines, citric acids, lactic acid, hydrochloric acid, calcium hydroxides, magnesium aluminometasilicates, and or any combinations thereof.

Examples of pharmaceutically acceptable buffers include but are not limited to sodium phosphate buffer (either sodium phosphate tribasic, sodium phosphate dibasic, sodium phosphate monobasic, or o-phosphoric acid), potassium phosphate buffers, and the like.

In certain preferred embodiments, the formulation further comprises a pharmaceutically acceptable complexing agent. The complexing agent is preferably included in an amount sufficient to inhibit the precipitation of drug substance (e.g., glucocorticoid) from the solvent (e.g., aqueous medium). "Complexing agents" are small molecular weight molecules which can form an inclusion complex and after suitable curing time, can solubilize the drug and may impart additional stability to the drug. Accordingly, for purposes of the present invention, the term "complexing agent" is meant to encompass agents that complex and/or solubilize a water-insoluble statin. In certain embodiments of the present invention, the pharmaceutically acceptable complexing agent is a dextrin. Other suitable dextrins include cyclodextrins such as hydroxy-propyl-β-cyclodextrin and sulfobutyl-ether-β-cyclodextrin. Additional cyclodextrins could include alpha-cyclodextrins, beta-cyclodextrins, gamma-cyclodextrins, beta-cyclodextrin ether comprising one or more hydroxybutyl sulfonate moieties and cyclodextrins as described in U.S. Pat. Nos. 6,610,671 or 6,566,347 (both of which are incorporated by reference). Additional complexing agents include, but are not limited to, the group consisting of phenol, phenolic salts, aromatic acids and esters, carboxylic acids and salts and esters thereof, inorganic acids and bases and amino acids and esters and salts thereof: methylparaben, propylparaben, potassium methylparaben, parabens, ascorbic acid and its derivatives, methyl anthranilate, salicylic acid, acetosalicyclic acid, tocopherol, organic acids, carboxylic acids, aromatic acids, aromatic esters, acid salts of amino acids, benzaldehyde, cinnimaldehyde, imidazole, menthol, thiophenol, m-aminobenzoic acid, anthranilic acid, picolinic acids and alkyl esters thereof, toluidides, sodium benzoate, sodium metabisulphite, malic acid, isoascorbic acid, citric acid, tartaric acid, sodium sulphite, sodium bisulphate, water- and fat-soluble derivatives of tocopherol, sulphites, bisulphites and hydrogen sulphites, propyl/gallate, nordihydroguaiaretic acid, phosphoric acids, sorbic and benzoic acids, methylparaben, sodium methylparaben, para-aminobenzoic acid and esters, sorbic and benzoic acids, 2,6-di-t-butyl-alpha-dimethyl-amino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, esters, isomeric compounds thereof, pharmaceutically acceptable salts thereof, and mixtures of any of the foregoing.

In certain embodiments of the present invention, the complexing agent comprises at least 0.1% of the formulation. In other preferred embodiments, the complexing agent comprises from about 0.05 to about 50% of the formulation, by weight. In certain preferred embodiments, the complexing agent is included in the solid formulation prior to reconstitution.

The liquid dosage forms of the invention for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and the like.

In certain preferred embodiments, the formulation of the invention includes one or preservatives, e.g., more antimicrobial agents in bacteriostatic or fungistatic concentrations. Typically, such agents are added where the formulation is packaged in multiple dose containers. Examples of pharmaceutically acceptable antimicrobial agents include phenols or cresols, mercurials, benzyl alcohol, chlorobutanol, methyl and propyl p hydroxybenzoic acid esters, thimerosal, benzalkonium chloride and benzethonium chloride, chlorinated phenolic compounds, alcohols, quaternary compounds, boric acid, benzoic acid, sodium benzoate and mixtures of any of the foregoing.

In certain embodiments, the liquid formulation further comprises one or more suspending and dispersing agents. Examples of suitable agents include sodium carboxymethylcelluose, hydroxypropyl methylcellulose and polyvinylpyrrolidone. Emulsifying agents include Polysorbate 80 (TWEEN® 80).

The liquid formulation preferably includes or consists of an aqueous carrier (e.g., water), although in certain embodiments the carrier may comprise a hydroalcoholic carrier. Pharmaceutical carriers also include, by way of example and without limitation, ethyl alcohol, polyethylene glycol and propylene glycol for water miscible vehicles. In certain preferred embodiments, the solvent concentration is from about 20 to about 99%, by weight.

In certain embodiments of the invention, the liquid formulation is lyophilized for later reconstitution prior to administration. On the other hand, the formulation can be prepared as a dry pre-mix powder. In preferred embodiments of the invention, the lyophilized particles comprising the glucocorticoid are stable. By "stable", it is meant that substantially no degradation of the dry mix and or lyophilized particles (the product) is observed after storage for 1 month at 40° C. In preferred embodiments, the term "stable" with respect to the dry mix and or lyophilized particles comprising the water-insoluble statin and complexing agent means that there is less than about 0.1% degradation observed) after storage for 1 month at 40° C.

In most applications, optimal viscosities of the system of the invention will range from about 0.25 to about 200,000 centipoise, preferably from about 0.3 to 1000 centipoise, and more preferably from about 0.5 to about 100 centipoise, at 37° C. While the benefit of the invention is realized over a broad range of elevated viscosities, the optimal viscosities will be different for different applications. The desired viscosity for any given formulation or use may vary, for example, according to the preference of the physician, the manner of application and type of applicator used, the amount of formulation needed, the area to which the formulation is to be applied, and similar considerations.

In certain embodiments, the invention is directed to a method of treating neurological disorder in particular for the treatment of Ataxia. In preferred embodiments, at least 90% of the liquid droplet size is more than 10 microns in order to prevent the inhalation of glucocorticoid into the lungs.

The present invention delivers and releases medicament in the form of small droplets, co-administration of water is not required thus making the oral spray formulation highly suitable for pediatric and geriatric patients who need frequent or immediate medical intervention. The oral spray composition can be sprayed over the tongue by using a metered dose spray pump that will deliver a composition preferably between the ranges of from about 40 microliters to about 350 microliters.

The daily dose of active ingredient (e.g., glucocorticoid) can administered as a single dose. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, pharmacological considerations, half-life of the drug, and eventual concomitant therapy with other drugs. In some instances, dosage levels below or above the aforesaid range and/or more frequent may be adequate, and this logically will be within the judgment of the physician and will depend on the disease state.

Spray systems are particularly useful for delivering therapeutics to the upper alimentary canal. Suitable spray delivery systems include both pressurized and non-pressurized (pump actuated) delivery devices. The glucocorticoid steroid(s) containing solution, delivered as an oral spray, is preferably an aqueous solution; however, organic and inorganic components, emulsifiers, excipients, and agents that enhance the organoleptic properties (i.e., flavoring agents or odorants) may be included. Optionally, the solution may contain a preservative that prevents microbial growth (i.e., sodium benzoate). Although water itself may make up the entire carrier, typical liquid spray formulations contain a co-solvent, for example, propylene glycol, corn syrup, glycerin, sorbitol solution and the like, to assist solubilization and incorporation of water-insoluble ingredients. In general, therefore, the compositions of this invention preferably contain from about 1-95% v/v and, most preferably, about 5-50% v/v, of the co-solvent.

The spray delivery system is normally designed to deliver from about 40 to about 350 microliters per actuation, and therapy may require from about 1 to about 10 actuations per dose. The rheological properties of the spray formulation are optimized to allow shear and atomization for droplet formation. Additionally, the spray delivery device is designed to create a droplet size which promotes retention on mucosal surfaces of the upper alimentary canal and minimize respiratory exposure. The present invention preferably minimizes the errors related to dosing accuracy of solutions delivered by an oral dropper device. Dose accuracy is critical to therapeutic efficacy when delivering small volumes and large volumes of oral liquids for in children. Ease of administration, increased compliance for patients who have difficulty swallowing solid oral dosage forms and large volumes of liquid formulation. The formulations of the invention preferably have the advantage of permitting dose titration, should this be desired based on patient weight and minimize errors related to the accuracy of dosing when compared to marketed devices e.g. oral droppers.

As previously mentioned, in certain embodiments the stable liquid pharmaceutical formulation of the present invention is an oral spray formulation that is used to treat a neurological disorder or disease in mammals (humans), such as ataxia. In this disease state, it is difficult for many patients to swallow, and administration of an oral liquid dose of glucocorticoid requires the patient to swallow a significant volume of liquid. The stable oral formulations allow for the reduction of liquid volume from about 15-20 ml for a unit dose to a fraction of that, i.e., from about 1 to about 5 sprays (e.g., each spray about 0.14 ml) of a unit dose of an aqueous solution of the disodium phosphate salt of betamethasone. Administered as an oral spray by actuating an oral spray device and delivering the formulation as a spray over the tongue of the patient, the formulation of the present invention eliminates the need for the patient to swallow the dose. The administered dose is absorbed in the gastrointestinal tract. It may be dosed as per mg drug/kg weight of the patient. It is particularly useful in the pediatric patient population.

In certain preferred embodiments, the stable oral liquid formulation has a concentration of the disodium salt of the glucocorticoid from about 0.25 mg/ml to about 12 mg/ml, wherein each spray has a liquid volume from about 0.040 ml to about 0.350 ml and the unit dose is delivered in from about 1 to about 20 sprays. In certain preferred embodiments, each spray has a liquid volume from about 0.040 ml to about 0.350 ml, and preferably about 0.14 ml. In embodiments in which the glucocorticoid is the disodium phosphate salt of betamethasone and each spray has a liquid volume of about 0.14 ml, the dose of betamethasone is delivered to the human patient in e.g., from about 1 to about 5 sprays. In certain preferred embodiments, the concentration of the solubilized glucocorticoid is preferably from about 0.33 mg/0.14 ml to about 1.32 mg/0.14 ml, or to about 1.65 mg/0.14 ml.

The oral spray formulations of the present invention are also particularly useful in asthmatic patients.

In certain preferred embodiments of the invention, the dose of betamethasone is titrated until steady-state is achieved. In such embodiments, the dose of the oral betamethasone spray formulation during a titration phase is from about 0.01 to about 0.2 mg/kg patient body weight administered once over a 12 hour and or 24 hour period. This translates to a betamethasone dose from about 0.07 mg to about 28 mg total per day, based on an average adult weighing 70 kg (based on betamethasone base). In other embodiments, the betamethasone dose may be from about 0.07 mg to about 14 mg for once daily dosing (every 24 hours) and from about 0.14 mg to about 28 mg for twice-a-day dosing (every 12 hours), based on an average adult weighing 70 kg (based on betamethasone base). The titration period may be, e.g., from about 2 to about 4 weeks, until steady-state is achieved. The dose can be further titrated based on the individual patient response. The dose of the oral betamethasone spray formulation at steady-state in such embodiments is preferably from about 0.02 to about 0.1 mg/kg patient body weight administered once over a 12 hour and or 24 hour period.

It is recognized by those having ordinary skill in the art that the dose of glucocorticoid is easily adjustable depending on the choice of particular glucocorticoid. For example, for the purpose of comparison, the following is an equivalent mg dosage of the preferred glucocorticoids of the invention: betamethasone 0.75 mg/dexamethasone 0.75 mg/triamcinolone 4 mg/prednisolone 5 mg/methylprednisolone 4 mg/hydrocortisone 20 mg. Therefore, although the doses of glucocorticoid presented above are based on betamethasone, a person having ordinary skill in the art would use the above information to calculate equivalent doses of one of the other (preferred) glucocorticoids if another glucocorticoid is to be administered to the patient.

It is known that in order for particles/droplets administered orally to get into the lungs of a human patient, the particles/droplets must be less than about 5 microns in diameter. Therefore, it is preferred that the oral spray formulation of the present invention provides droplets that are greater in size than 5 microns, and in preferred embodiments no more than about 10% of the droplets should be below 10 microns in diameter. In certain preferred embodiments of the invention, not more than about 0.5% of the droplets are below 10 microns in diameter.

DETAILED DESCRIPTION OF THE PREFERRED EMBODIMENTS

The following examples illustrate various aspects of the present invention. They are not to be construed to limit the claims in any manner whatsoever.

Example 1

A betamethasone liquid formulation is prepared using the ingredients set forth in Table 1.

TABLE 1

| Composition | Example 1 mg/spray |
|---|---|
| Betamethasone disodium phosphate | 1.32 |
| Citric acid | 0.60 |
| Sorbitol | 6.00 |
| Sodium benzoate | 0.18 |
| Flavor | 0.24 |
| Purified Water | Qs |

The formulation is prepared as follows: Add betamethasone to purified water while stirring and mix till a clear solution is observed. Add preservative, buffering agent and other excipients while stirring and mix for 30 minutes till a clear solution is formed. Store the solution in a glass bottle with cap or metered dose mechanical pump.

The formulation of Example 1 has the advantage of permitting dose titration, should this be desired, based on the patient weight. An added advantage is that the volume of solution administered to achieve therapeutic efficacy is less than 1 ml, which can administer with great accuracy using a metered dose pump spray. Each spray contains 1.32 mg of betamethasone sodium phosphate and a total volume of 0.14 ml.

The oral spray droplet size distribution of Example 1 is set forth in Table 2 and FIG. 1 (average droplet size distribution plot of Example 1).

TABLE 2

Betamethasone Oral Spray

| Unit ID | Dv(10), μm | Dv(50), μm | Dv(90), μm | % Droplets <10 μm | Pump Delivery (mg) |
|---|---|---|---|---|---|
| Example 1 (n-1) | 23.95 | 60.92 | 126.2 | 0.290 | 142.5 |
| Example 1 (n-2) | 24.11 | 64.29 | 139.3 | 0.093 | 141.0 |
| Example 1 (n-3) | 22.43 | 57.55 | 127.5 | 0.141 | 139.7 |
| Mean | 23.50 | 60.92 | 131.0 | 0.175 | 141.1 |
| SD | 0.93 | 3.37 | 7.2 | 0.10 | 1.4 |
| % CV | 3.9 | 5.5 | 5.5 | 58.8 | 1.0 |

Table 3 below provides the number of sprays required every 12 hours based on the patient's body weight for the formulation of Example 1.

TABLE 3

| Weight (kg) | Full Dose (0.1 mg/kg/day) | | | Titrated Dose (0.05 mg/kg/day) | | |
|---|---|---|---|---|---|---|
|  | 0.25 mg/spray | 0.5 mg/spray | 1 mg/spray | 0.25 mg/spray | 0.5 mg/spray | 1 mg/spray |
| 10-19 | 3 | | | 1 | | |
| 20-29 | | 2 | | | 1 | |
| 30-39 | | 3 | | 3 | | |
| 40-49 | | | 2 | | | 1 |
| 50-59 | | | 3 | | 3 | |
| 60-70 | | | 3 | | 3 | |

Examples 2-3

A betamethasone liquid spray formulation is prepared using the ingredients set forth in Table 4.

TABLE 4

| Composition | Example 2 mg/spray | Example 3 mg/spray |
|---|---|---|
| Glucocorticoid (betamethasone disodium phosphate) | 0.66 | 0.33 |
| Citric acid | 0.60 | 0.60 |
| Sorbitol | 6.00 | 6.00 |
| Sodium benzoate | 0.18 | 0.18 |
| Flavor | 0.24 | 0.24 |
| Purified Water | Qs | Qs |

The formulation is prepared as follows: Add glucocorticoid steroid in purified water while stirring and mix till a clear solution is observed. Add preservative, buffering agent and other excipients while stirring and mix for 30 minutes till a clear solution is formed. Store the solution in a glass bottle with cap or metered dose mechanical pump.

Example 4

Examples 4 and 4b are dry mixes for reconstitution (as is or lyophilized). The ingredients are set forth in Table 5 below. The xanthan gum is Example 4b is included as a thickening agent.

TABLE 5

| Composition | Example 4a g | Example 4b g |
|---|---|---|
| Glucocorticoid (betamethasone disodium phosphate) | 0.66 | 0.33 |
| Xanthan gum | | 0.15 |
| Citric acid | 0.60 | 0.60 |
| Sorbitol | 6.00 | 6.00 |
| Sodium benzoate | 0.18 | 0.18 |
| Flavor | 0.24 | 0.24 |

Example 5

A betamethasone oral syrup formulation is prepared using the ingredients set forth in Table 6 below. The formulation is prepared as follows: Add betamethasone to purified water while stirring and add sorbitol and mix until a syrup is formed. Add preservative, buffering agent and other excipients while stirring and mix for 30 minutes till a clear solution is formed. Store the solution in a glass bottle with cap.

TABLE 6

| Composition | Example 5 g |
|---|---|
| Glucocorticoid (betamethasone disodium phosphate) | 0.66 |
| Citric acid | 0.60 |
| Sorbitol | 55.00 |
| Sodium benzoate | 0.18 |
| Flavor | 0.24 |
| Purified water | qs |

Example 6

As shown in Table 7, the previously approved or available dose offered by Celestone oral liquid (betamethasone solution 0.5 mg/5 mL) results in administrating about 4 ml to 30 ml of solution every 12 hours to a pediatric patient based on body weight. Most pediatric AT patients have difficulty swallowing large volumes of liquid due to lack of muscle control during voluntary movements and affects swallowing thus leading to underdose or overdose when swallowing large volumes of liquid. The betamethasone spray formulation of the present invention provides a high loading dose of betamethasone up to 1 mg per 0.140 ml spray solution that delivers a precise and accurate amount of drug every dosing period. The volume of spray solution required every 12 hours is about 0.14 ml to 0.42 ml (1 to 3 sprays) based on patient body weight. The present invention importantly allows the patient or healthcare professional to choose the number of sprays to administer to achieve the correct or optimal dose for the particular body weight of the patient (Table 7). This can be achieved either by administrating several sprays from a multi-dose pump device or several single use pumps. The proposed betamethasone drug product dose range for pediatric AT is from about 0.025 to about 0.1 mg/kg/day.

TABLE 7

Comparison of Celestone and the invented oral spray formulation volume of administered every 12 hours based on body weight

| Weight of patient, kg | Max Betamethasone per 12 hours, mg | Approved Product Celestone, 0.6 mg/5 ml | Proposed Drug Product, (0.25 or 0.5 or 1.0 mg/ spray) |
|---|---|---|---|
| 10 | 0.5 | 4.2 ml | 0.42 ml |
| 20 | 1.0 | 8.3 ml | 0.42 ml |
| 30 | 1.5 | 12.5 ml | 0.42 ml |
| 40 | 2.0 | 16.7 ml | 0.42 ml |
| 50 | 2.5 | 20.8 ml | 0.42 ml |
| 60 | 3.0 | 25.0 ml | 0.42 ml |
| 70 | 3.5 | 29.2 ml | 0.42 ml |

The present oral spray invention reduces dose volume administered every twelve hours by more than 90 volume percentage (Table 7) thus facilitating ease of use and compliance by the pediatric AT patient who find it difficult to swallow large volumes of liquid.

Example 7

The formulation of Example 1, 2 and 3 was filled in the 5 ml amber glass bottles with screw cap closure and subjected to stability studies under the following conditions:
ICH accelerated condition at 40° C.±2° C./75% RH±5% RH;
ICH room temperature condition at 25° C.±2° C./60% RH±5% RH; and
ICH refrigeration condition at 5° C.±3° C.

Samples were analyzed to measure the percentage of betamethasone base conversion in the formulation at different temperatures over time. Also physical stability of the invented formulation example, precipitation of betamethasone in solution and pH drift was recorded.

TABLE 8

Example - 1 Betamethasone oral spray
(betamethasone sodium phosphate 1.32 mg per 0.14 ml spray)

| | | 40° C. ± 2° C./75% RH ± 5% RH | | | | 25° C. ± 2° C./ 60% RH ± 5% RH | | |
|---|---|---|---|---|---|---|---|---|
| | Initial | 1 M | 2 M | 3 M | 6 M | 1 M | 2 M | 3 M |
| Appearance | Clear colorless solution | C | C | — | — | C | C | C |
| Total betamethasone, Assay % | 104.01 | 101.27 | 98.15 | NC | — | 104.69 | 101.46 | 101.54 |
| Betamethasone base, Area % | <LOQ | 4.56 | 6.96 | >10 | — | 0.45 | <LOQ | <LOQ |
| Total impurities, % | <LOQ | <LOQ | <LOQ | <LOQ | — | <LOQ | <LOQ | <LOQ |
| Physical stability | Stable | Stable | Stable | Not stable | Not Stable | Stable | Stable | Stable |

| | 25° C. ± 2° C./ 60% RH ± 5% RH | | | 5° C. ± 3° C. | | | | |
|---|---|---|---|---|---|---|---|---|
| | 6 M | 9 M | 12 M | 1 M | 3 M | 6 M | 9 M | 12 M |
| Appearance | C | C | C | C | C | C | C | C |
| Total betamethasone, Assay % | 95.17 | 99.06 | 99.70 | 104.53 | 106.14 | 96.15 | 104.93 | 103.58 |
| Betamethasone base, Area % | 2.10 | 3.18 | 4.78 | 0.06 | <LOQ | <LOQ | <LOQ | <LOQ |
| Total impurities, % | <LOQ | <LOQ | <LOQ | <LOQ | <LOQ | <LOQ | <LOQ | <LOQ |
| Physical stability | Stable | Stable | Stable | Stable | Stable | Stable | Stable | Stable |

C: Complies,
NC: Not Complies,
LOQ: Limit below quantification
Not Stable: Betamethasone base precipitated in the formulation
M = months storage

TABLE 9

Example - 2 Betamethasone oral spray
(betamethasone sodium phosphate 0.66 mg per 0.14 ml spray)

|  | Initial | 40° C. ± 2° C./75% RH ± 5% RH | | | | 25° C. ± 2° C./60% RH ± 5% RH | | |
| --- | --- | --- | --- | --- | --- | --- | --- | --- |
|  |  | 1 M | 2 M | 3 M | 6 M | 1 M | 2 M | 3 M |
| Appearance | Clear colorless solution | C | C | — | — | C | C | C |
| Total betamethasone, Assay % | 104.81 | 100.01 | 97.89 | NC | — | 103.22 | 100.65 | 105.04 |
| Betamethasone base, Area % | <LOQ | 3.97 | 7.00 | >10 | — | 0.58 | <LOQ | <LOQ |
| Total Impurities, % | <LOQ | <LOQ | <LOQ | <LOQ | — | <LOQ | <LOQ | <LOQ |
| Physical stability | Stable | Stable | Stable | Not stable | Not Stable | Stable | Stable | Stable |

|  | 25° C. ± 2° C./60% RH ± 5% RH | | | 5° C. ± 3° C. | | | | |
| --- | --- | --- | --- | --- | --- | --- | --- | --- |
|  | 6 M | 9 M | 12 M | 1 M | 3 M | 6 M | 9 M | 12 M |
| Appearance | C | C | C | C | C | C | C | C |
| Total betamethasone, Assay % | 95.42 | 102.14 | 98.91 | 103.76 | 106.10 | 103.77 | 103.13 | 103.82 |
| Betamethasone base, Area % | 2.14 | 3.13 | 4.52 | 0.05 | <LOQ | <LOQ | <LOQ | <LOQ |
| Total Impurities, % | <LOQ | <LOQ | <LOQ | <LOQ | <LOQ | <LOQ | <LOQ | <LOQ |
| Physical stability | Stable | Stable | Stable | Stable | Stable | Stable | Stable | Stable |

C: Complies,
NC: Not Complies,
LOQ: Limit below quantification
Not Stable: Betamethasone base precipitated in the formulation
M = months storage

TABLE 10

Example - 3 Betamethasone oral spray
(betamethasone sodium phosphate 0.33 mg per 0.14 ml spray)

|  | Initial | 40° C. ± 2° C./75% RH ± 5% RH | | | | 25° C. ± 2° C./60% RH ± 5% RH | | |
| --- | --- | --- | --- | --- | --- | --- | --- | --- |
|  |  | 1 M | 2 M | 3 M | 6 M | 1 M | 2 M | 3 M |
| Appearance | Clear colorless solution | C | C | C | — | C | C | C |
| Total betamethasone, Assay % | 105.81 | 99.70 | 96.55 | 94.61 | — | 103.60 | 101.78 | 101.75 |
| Betamethasone base, Area % | <LOQ | 3.96 | 7.03 | 10.40 | — | 0.48 | <LOQ | 1.20 |
| Total Impurities, % | <LOQ | <LOQ | <LOQ | <LOQ | — | <LOQ | <LOQ | <LOQ |
| Physical stability | Stable | Stable | Stable | Stable | Not Stable | Stable | Stable | Stable |

|  | 25° C. ± 2° C./60% RH ± 5% RH | | | 5° C. ± 3° C. | | | | |
| --- | --- | --- | --- | --- | --- | --- | --- | --- |
|  | 6 M | 9 M | 12 M | 1 M | 3 M | 6 M | 9 M | 12 M |
| Appearance | C | C | C | C | C | C | C | C |
| Total betamethasone, Assay % | 93.98 | 99.40 | 102.28 | 103.63 | 103.13 | 96.37 | 101.67 | 105.06 |
| Betamethasone base, Area % | 2.11 | 3.22 | 4.41 | 0.06 | <LOQ | <LOQ | <LOQ | <LOQ |

TABLE 10-continued

Example - 3 Betamethasone oral spray
(betamethasone sodium phosphate 0.33 mg per 0.14 ml spray)

| Total Impurities, % | <LOQ | <LOQ | <LOQ | <LOQ | <LOQ | <LOQ | <LOQ | <LOQ |
|---|---|---|---|---|---|---|---|---|
| Physical stability | Stable | Stable | Stable | Stable | Stable | Stable | Stable | Stable |

Figure 2:
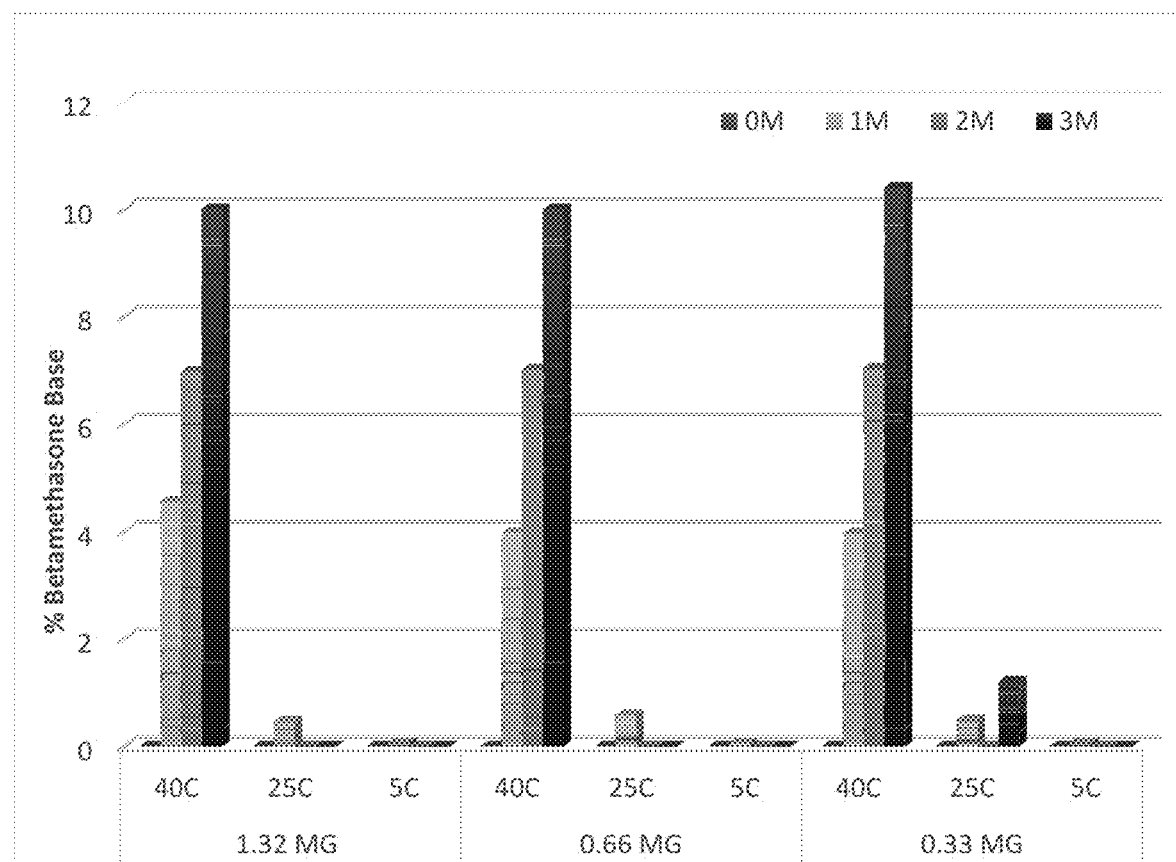
FIG. 2 is a graph depicting the percentage betamethasone base conversion when formulation stored at different temperatures for Example 7.

C: Complies,
NC: Not Complies,
LOQ: Limit below quantification
Not Stable: Betamethasone base precipitated in the formulation
M = months storage From the data provided in Tables 8, 9, 10 and FIG. 2 (percentage betamethasone base conversion when formulation stored at different temperatures) it can be concluded that present invented oral spray solution of betamethasone sodium phosphate is stable at room temperature and below room temperature. Also it was observed that percentage of betamethasone base conversion in the formulation increases with temperature and time. The precipitation of betamethasone base in the formulation was observed when it is composes more than 10% of total betamethasone in the formulation.

Example 8

In-Vivo Study

An in-vivo study was performed in healthy rabbits to evaluate drug release from a betamethasone oral spray made in accordance with Example 3. A single dose crossover study to evaluate the pharmacokinetics and relative bioavailability of 0.25 mg betamethasone per spray (oral spray formulation), 0.14 ml per spray and 0.25 mg per 2 ml of betamethasone oral solution (equivalent to previously approved formulation). The pharmacokinetics study was performed in 6 healthy rabbits (3 males and 3 females). The reference product was a single 0.25 mg dose (2 ml) of betamethasone base administered orally with the help of oral gavage. The test formulation was a betamethasone sodium phosphate 0.33 mg oral spray (equivalent to 0.25 mg betamethasone base and 0.1 mg/kg dose) administered as a single spray in the oral cavity (over the tongue) using a metered dose spray pump. Blood samples were collected at 30 minutes, 1, 2, 3, 4, 6, 8, 12 and 24 hours post dose. All samples were analyzed using a validated analytical LC-MS method.

From a single oral spray dose application, the mean $C_{max}$ was found to be 158.17 ng/mL at median $T_{max}$ of 2.0 hr. The mean $AUC_{0-t}$ and $AUC_{0-infinity}$ was found to be 851.16 and 866.02 ng*hr/mL, respectively. The mean elimination half-life was found to be 3.19 hr. The clearance and volume of distribution were 5.30 mL/min and 1.77 L, respectively. The relative bioavailability was found to be 121.13% relative to reference oral solution (equivalent to previously approved formulation).

From a single oral solution dose application, the mean $C_{max}$ was found to be 82.63 ng/mL at median Tmax of 3.0 hr. The $AUC_{0-t}$ and $AUC_{0-infinity}$ was found to be 709.29 and 729.40 ng*hr/mL, respectively. The mean elimination half-life was found to be 3.93 hr. The clearance and volume of distribution were 6.11 mL/min and 2.00 L, respectively.

Figure 3:
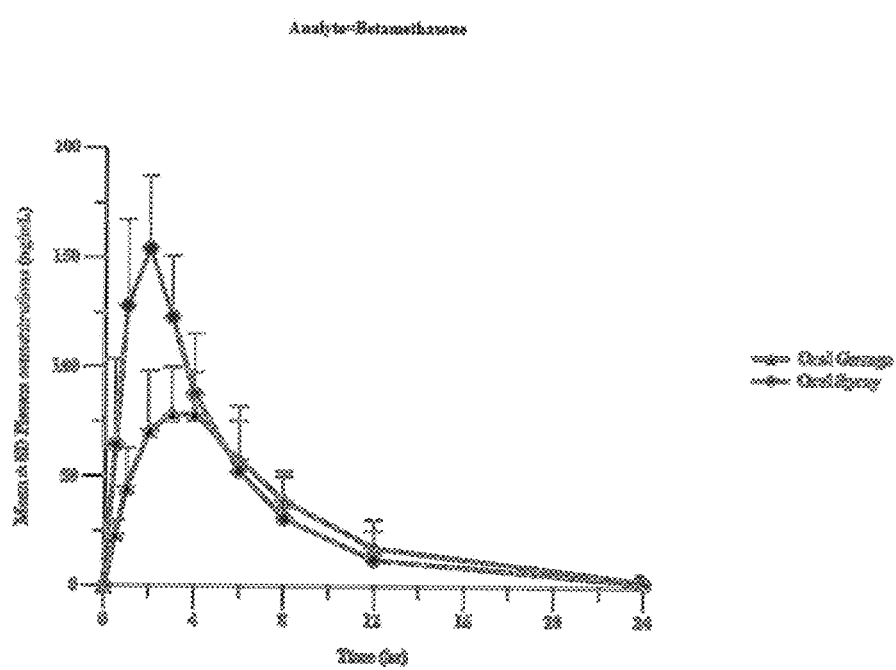
FIG. 3 is a graph depicting mean plasma concentration-time profile of betamethasone following reference (oral solution) and oral spray of the invention (Example 3) oral route of administration in rabbits.

The pharmacokinetic results are reported in Table 11 and FIG. 3 (mean plasma concentration-time profile of betamethasone following reference (oral solution) and oral spray of the invention (Example 3) oral route of administration in rabbits).

TABLE 11

Mean plasma pharmacokinetic parameters of Betamethasone following a single oral (two different formulations; oral spray and oral solution) route of administration in rabbits.

| | Group/Formulation | |
|---|---|---|
| | Group 1, Oral Spray | Group 2, Oral Solution |
| | Dose/ROA | |
| Pk Parameters | 0.25 mg/rabbit, Oral Spray | 0.25 mg/rabbit, Oral solution |
| $C_{max}$ (ng/mL) | 158.17 ± 31.30 (20) | 82.63 ± 23.06 (28) |
| $T_{max}$ (hr) [a] | 2.0 (1.0-3.0) | 3.0 (2.0-4.0) |
| $AUC_{0-t\ hr}$ (ng*hr/mL) | 851.16 ± 314.19 (37) | 709.29 ± 193.51 (27) |
| $AUC_{0-infinity}$ (ng*hr/mL) | 866.02 ± 336.77 (39) | 729.40 ± 217.86 (30) |
| Kel (1/hr) | 0.19 ± 0.04 (23) | 0.19 ± 0.06 (29) |
| $t_{1/2}$ (hr) | 3.19 ± 0.91 (23) | 3.93 ± 1.21 (31) |
| CL/F (mL/min) | 5.30 ± 1.59 (30) | 6.11 ± 1.67 (27) |
| $V_z$/F (L) | 1.77 ± 0.64 (36) | 2.00 ± 0.52 (26) |
| Relative Bioavailability (% F) | 121.13 ± 27.68 (23) | — |

Values are mean ± SD (% CV), n = 6 rabbits/group.
[a] $T_{max}$ reported as median (min-max)

There was a 1.9 fold increase in plasma exposure ($C_{max}$) to betamethasone and the absorption was rapid in the oral spray formulation when compared to the reference oral solution. The AUC's of invented oral spray were increased by 20% when compared with reference oral solution. The remaining pharmacokinetic parameters (e.g., clearance, half life, volume of distribution of oral spray and oral solutions) were similar in both the products. From this study, it can be concluded that the (e.g., over-the-tongue) oral spray formulation invented increases the rate and extent of betamethasone absorption compared to approved oral solution formulation.

Example 9

Respective salt and base forms of betamethasone and dexamethasone were weighed and transferred in the glass test tube. Water was added in the test tube using micro pipet and mixed for 5 minutes using mechanical vortex and the solubility of the betamethasone was assessed. The results are presented in Table 12 below.

TABLE 12

|  | Concentration mg/0.14 ml | Solubility in purified water |
|---|---|---|
| Betamethasone disodium phosphate | 0.25 mg/0.14 ml | Soluble |
|  | 0.50 mg/0.14 ml | Soluble |
|  | 1.00 mg/0.14 ml | Soluble |
|  | 1.50 mg/0.14 ml | Soluble |
|  | 2.00 mg/0.14 ml | Soluble |
|  | 4.00 mg/0.14 ml | Soluble |
|  | 8.00 mg/0.14 ml | Soluble |
| Betamethasone Acetate | 0.25 mg/0.14 ml | Not Soluble |
| Betamethasone base | 0.25 mg/0.14 ml | Not Soluble |
| Dexamethasone disodium phosphate | 1.00 mg/0.14 ml | Soluble |
|  | 2.00 mg/0.14 ml | Soluble |
|  | 4.00 mg/0.14 ml | Soluble |
|  | 8.00 mg/0.14 ml | Soluble |
| Dexamethasone base | 0.25 mg/0.14 ml | Not Soluble |

Example 10

Figure 4:
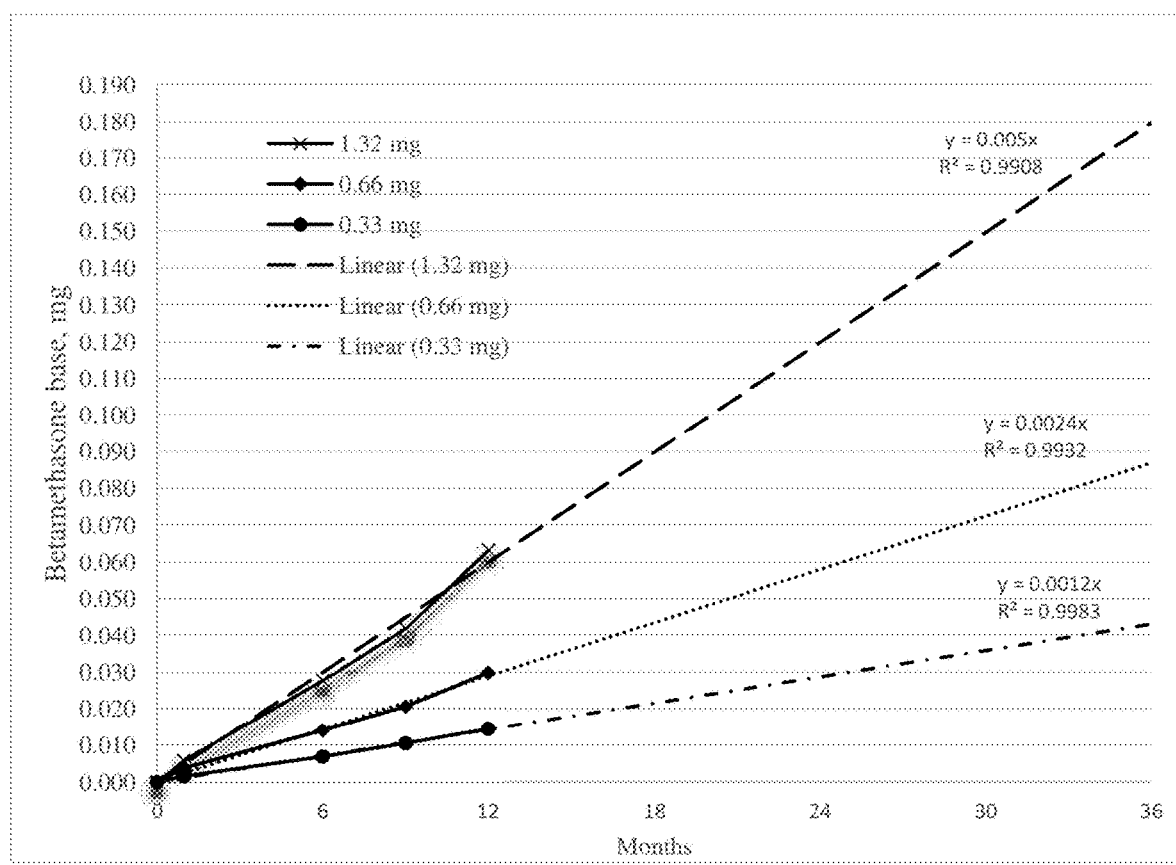
FIG. 4 is a graph depicting a prediction of betamethasone base conversion over time at 25° C. for Examples 1, 2 and 3.

The amount of betamethasone base converted from the disodium phosphate salt when the aqueous oral spray formulation is stored at 25° C. up to 12 months on stability is reported in Table 13. As show in FIG. 4 (prediction of betamethasone base conversion over time at 25° C.), a linear regression statistical tool is used to predict the amount of betamethasone base formed over the drug product shelf life (24 and or 36 months). From the accelerated stability study data, we conclude that betamethasone base precipitates out in the oral spray formulation when it converts to more than 0.15 mg/0.14 ml (spray volume)(equivalent to 1.07 mg/ml).

TABLE 13

Betamethasone base converted at 25° C. during stability, mg

| Time points, months | Example 1 1.32 mg/spray | Example 2 0.66 mg/spray | Example 3 0.33 mg/spray |
|---|---|---|---|
| 0 | 0.000 | 0.000 | 0.000 |
| 1 | 0.006 | 0.004 | 0.002 |
| 6 | 0.028 | 0.014 | 0.007 |
| 9 | 0.042 | 0.021 | 0.011 |
| 12 | 0.063 | 0.030 | 0.015 |

Based on predictive linear regression data, it can be concluded that the higher strength of 1.32 mg per spray oral spray formulation will be stable up to 24 months and other two strengths (0.33 mg and 0.66 mg) will be stable up to 36 months at 25° C.

Figure 5:
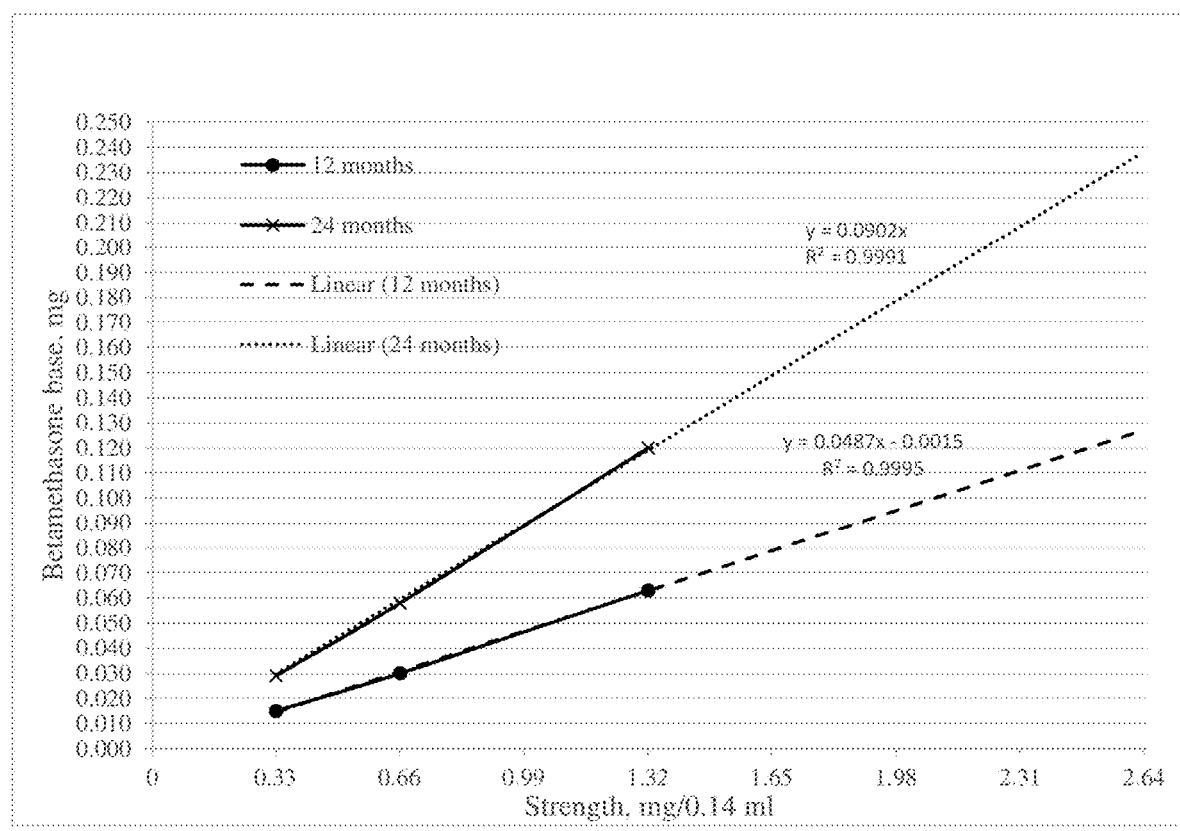
FIG. 5 is a graph depicting a prediction of betamethasone base conversion over time at 25° C. at higher drug concentrations.

Table 14 and FIG. 5 (prediction of betamethasone base conversion over time at 25° C. at higher drug concentration) show the stability of different drug concentration per spray in oral spray formulation with respect to time using the linear regression statistical tool, when stored at 25° C.

TABLE 14

Betamethasone base (in mg) converted at 25° C. at 12 and 24 months

|  | 12 months | 24 months (Predicted value using linear regression) |
|---|---|---|
| 0.33 | 0.015 | 0.029 |
| 0.66 | 0.030 | 0.058 |
| 1.32 | 0.063 | 0.120 |

Based on the above data it can be concluded that the aqueous oral spray formulation of betamethasone will be stable for 24 months as a clear solution at a concentration of up to 1.65 mg of betamethasone disodium phosphate per spray of 0.14 ml solution.

Example 11

Dexamethasone liquid spray formulations are prepared using the ingredients set forth in Table 15.

TABLE 15

| Composition | mg/spray | mg/spray |
|---|---|---|
| Dexamethasone disodium phosphate | 0.50 | 0.10 |
| Citric acid | 0.60 | 0.60 |
| Sorbitol | 6.00 | 6.00 |
| Sodium benzoate | 0.18 | 0.18 |
| Flavor | 0.24 | 0.24 |
| Purified Water | Qs | qs |

CONCLUSION

It will be readily apparent to one of ordinary skill in the relevant arts that other suitable modifications and adaptations to the methods and applications described herein are suitable and may be made without departing from the scope of the invention or any embodiment thereof.

While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

The invention claimed is:

1. A method for diminishing a neurological symptom associated with ataxia in a human patient, comprising orally administering to a human patient suffering from a neurological symptom associated with ataxia a stable oral liquid spray formulation consisting of a disodium salt of a glucocorticoid selected from the group consisting of betamethasone, dexamethasone, prednisolone, methylprednisolone, hydrocortisone and triamcinolone, and mixtures of any of the foregoing, water; a pH modifying agent and/or a buffer in an amount sufficient to adjust the pH of the formulation; and an optional pharmaceutically acceptable excipient selected from the group consisting of a preservative, a sweetener, a flavor, and a combination thereof; wherein when a preservative is included the preservative is in an amount effective to preserve the formulation and is selected from the group consisting of mercurials, methyl and propyl paraben, hydroxybenzoic acid esters, thimerosal, benzalkonium chloride and benzethonium chloride, quaternary compounds, boric acid, benzoic acid, sodium benzoate and mixtures of any of the foregoing, the disodium salt of the glucocorticoid being solubilized and less than 11% of the corresponding base form of the glucocorticoid, by spraying a unit dose of the glucocorticoid over the tongue of the human patient, the stable oral liquid formulation having a concentration of the disodium salt of the glucocorticoid from about 0.25 mg/ml to about 12 mg/ml, wherein each spray has a liquid volume from about 0.040 to about 0.350 ml and the unit dose is delivered in from about 1 to about 20 sprays from a mechanical spray device, and the oral liquid spray formulation is stable for at least about 24 months as a clear solution and without precipitate.

2. The method of claim 1, wherein the ataxia is ataxia telangiectasia.

3. The method of claim 1, wherein the spray is as a plume or a stream over the tongue.

4. The method of claim 1, wherein a single unit dose of the glucocorticoid is provided when from 1 to about 5 sprays are delivered into the mouth of the patient.

5. The method of claim 1, wherein the mechanical spray device provides multiple doses of the glucocorticoid.

6. The method of claim 1, wherein the glucocorticoid formulation when sprayed provides a droplet size from about 5 to about 500 microns.

7. The method of claim 6, wherein the oral spray droplet size of 90% of the liquid particles (Dv(90)) is 131 µm±30.

8. The method of claim 1, wherein the glucocorticoid is betamethasone.

9. The method of claim 1, further comprising storing the stable oral liquid formulation at a temperature from about 2° C. to about 25° C., such that the stable oral liquid formulation has a shelf life of at least 24 months.

10. The method of claim 1, wherein each spray has a volume of about 0.14 ml and each spray delivers from about 0.33 mg to about 1.65 mg glucocorticoid and the formulation is stable for at least about 24 months as a clear solution without precipitate.

11. The method of claim 1, wherein the concentration of glucocorticoid in the stable oral liquid formulation is from about 3.57 mg/ml to about 8.93 mg/ml EQ to the glucocorticoid base.

12. A method for diminishing a neurological symptom associated with ataxia in a human patient, comprising orally administering to a human patient suffering from a neurological symptom associated with ataxia a stable oral aqueous liquid formulation consisting of betamethasone disodium phosphate, water; optional pharmaceutically acceptable excipients selected from the group consisting of a preservative, a sweetener, a flavor, and a combination thereof; and a pH modifying agent and/or a buffer in an amount sufficient to adjust the pH of the formulation, the disodium salt of betamethasone disodium phosphate being solubilized; wherein the stable oral aqueous liquid formulation does not include an alcoholic solvent or a cyclodextrin, by spraying a unit dose of the stable oral liquid formulation over the tongue of the human patient, the stable oral liquid formulation having a concentration of the betamethasone disodium phosphate from about 0.25 mg/ml to about 12 mg/ml, wherein each spray has a liquid volume from about 0.040 to about 0.350 ml and the unit dose is delivered in from about 1 to about 7 sprays of the stable oral liquid formulation, and the stable oral aqueous liquid spray formulation is stable for at least about 24 months as a clear solution without precipitate.

13. The method of claim 12, wherein the concentration of the solubilized betamethasone disodium phosphate in the formulation is from about 3.57 mg/ml to about 8.93 mg/ml EQ to betamethasone.

14. The method of claim 12, wherein the concentration of glucocorticoid in the stable oral liquid formulation is from about 7.14 mg/ml to about 8.93 mg/ml EQ to the glucocorticoid base.

15. The method of claim 12, wherein the neurological disorder is ataxia telangiectasia.

16. The method of claim 12, wherein the spray is as a plume or a stream over the tongue.

17. The method of claim 12, wherein the formulation when sprayed provides a droplet size from about 5 to about 500 microns.

18. The method of claim 17, wherein the oral spray droplet size of 90% of the liquid particles (Dv(90)) is 131 µm±30.

19. The method of claim 12, wherein each spray delivers from about 0.33 mg to about 1.65 mg glucocorticoid.

20. The method of claim 9, wherein the pH of the stable oral liquid spray formulation is adjusted to a pH from about 3 to about 6 and the stable oral liquid spray formulation is supersaturated.

21. The method of claim 12, wherein the pH of the stable oral liquid spray formulation is adjusted to a pH from about 3 to about 6 and the stable oral liquid spray formulation is supersaturated.

22. A method for diminishing a neurological symptom associated with ataxia in a human patient, comprising orally administering to the human patient suffering from a neurological symptom associated with ataxia a stable oral liquid formulation of a disodium salt of a glucocorticoid consisting of a disodium salt of a glucocorticoid selected from the group consisting of betamethasone, dexamethasone, prednisolone, methylprednisolone, hydrocortisone and triamcinolone, and mixtures of any of the foregoing, a solvent which consists of water; optional pharmaceutically acceptable excipients selected from the group consisting of a preservative in an amount effective to preserve the formulation, a sweetener, a flavor, and a combination thereof, wherein the formulation does not include an alcoholic solvent or a cyclodextrin; and a pH modifying agent and/or a buffer in an amount sufficient to adjust the pH of the formulation, the disodium salt of the glucocorticoid being solubilized, by spraying a unit dose of the glucocorticoid over the tongue of the human patient, the stable oral liquid formulation having a concentration of the disodium salt of the glucocorticoid from about 0.25 mg/ml to about 12 mg/ml, wherein each spray has a liquid volume from about 0.040 to about 0.350 ml and the unit dose is delivered in from about 1 to about 20 sprays from a mechanical spray device, and the stable oral liquid spray formulation is stable for at least about 24 months as a clear solution without precipitate.

23. The method of claim 22, wherein the glucocorticoid is betamethasone.

24. The method of claim 22, wherein the pH is adjusted to a pH from about 3 to about 6 and the stable oral liquid spray formulation is supersaturated.

25. The method of claim 12, wherein the aqueous oral spray formulation of betamethasone is stable for about 24 months as a clear solution at a concentration of up to 1.65 mg of betamethasone disodium phosphate per spray of about 0.14 ml solution.

* * * * *